US012427245B2

(12) United States Patent
Katuin et al.

(10) Patent No.: US 12,427,245 B2
(45) Date of Patent: Sep. 30, 2025

(54) MEDICATION DELIVERY DEVICE WITH DOSE DETECTION SYSTEM

(71) Applicant: Eli Lilly and Company, Indianapolis, IN (US)

(72) Inventors: Joseph Edward Katuin, Cicero, IN (US); Sean Matthew Pszenny, Cambridge, MA (US); Oliver Brian Regele, Cambridge, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 876 days.

(21) Appl. No.: 17/266,423

(22) PCT Filed: Aug. 9, 2019

(86) PCT No.: PCT/US2019/045895
§ 371 (c)(1),
(2) Date: Feb. 5, 2021

(87) PCT Pub. No.: WO2020/036822
PCT Pub. Date: Feb. 20, 2020

(65) Prior Publication Data
US 2021/0290841 A1    Sep. 23, 2021

Related U.S. Application Data

(60) Provisional application No. 62/719,380, filed on Aug. 17, 2018.

(51) Int. Cl.
*A61M 5/145* (2006.01)
*A61M 5/172* (2006.01)
(Continued)

(52) U.S. Cl.
CPC .......... *A61M 5/1452* (2013.01); *A61M 5/172* (2013.01); *A61M 5/31528* (2013.01);
(Continued)

(58) Field of Classification Search
CPC .......... A61M 5/31568; A61M 5/31528; A61M 5/31566; A61M 5/31551; A61M 5/31585;
(Continued)

(56) References Cited

U.S. PATENT DOCUMENTS 5,704,922 A    1/1998    Brown
5,751,230 A *  5/1998    Brandestini .......... G01D 5/2492
                                                      341/16
(Continued)

FOREIGN PATENT DOCUMENTS

EP    3175876    6/2017
EP    2958612    11/2018
(Continued)

OTHER PUBLICATIONS

Office action issued by the Japanese Patent Office dated Mar. 1, 2022 pertaining to Japanese Patent Application 2021-507645.
(Continued)

*Primary Examiner* — Courtney B Fredrickson
*Assistant Examiner* — Kayla M. Turkowski
(74) *Attorney, Agent, or Firm* — Arthur Shum

(57) ABSTRACT

A medication delivery device is disclosed having a dose detection system and an associated control system configured to determine an amount of medication delivered from the medication delivery device based on the sensing of relative rotation within the medication delivery device. The relative rotation may occur between a dose setting member and an actuator and/or housing of the medication delivery device. The rotation sensing may involve sliding contact sensing. A latch circuit may be coupled between the rotational sensor and the controller. The dose detection system may be a modular or integral component of the medication delivery device.

16 Claims, 15 Drawing Sheets

(51) Int. Cl.
*A61M 5/31* (2006.01)
*A61M 5/315* (2006.01)

(52) U.S. Cl.
CPC .... *A61M 5/31546* (2013.01); *A61M 5/31568* (2013.01); *A61M 5/31573* (2013.01); *A61M 2005/3126* (2013.01); *A61M 2205/3327* (2013.01); *A61M 2205/52* (2013.01)

(58) Field of Classification Search
CPC ............ A61M 5/3155; A61M 5/31546; A61M 5/31573; G05B 2219/1164; H03M 1/24
See application file for complete search history.

(56) References Cited

U.S. PATENT DOCUMENTS

| | | | |
|---|---|---|---|
| 5,774,075 A * | 6/1998 | Palalau | H01H 19/585 345/184 |
| 6,277,099 B1 | 8/2001 | Strowe et al. | |
| 7,195,616 B2 | 3/2007 | Diller et al. | |
| 7,291,132 B2 | 11/2007 | DeRuntz et al. | |
| 8,221,356 B2 | 7/2012 | Enggaard et al. | |
| 8,734,394 B2 | 5/2014 | Adams et al. | |
| 9,186,465 B2 | 11/2015 | Jørgensen et al. | |
| 9,636,464 B1 | 5/2017 | Binier | |
| 9,649,448 B2 | 5/2017 | Madsen | |
| 9,833,576 B2 | 12/2017 | Windum et al. | |
| 2004/0210199 A1 | 10/2004 | Atterbury et al. | |
| 2009/0139325 A1 * | 6/2009 | Cunningham | G01D 5/24 73/304 C |
| 2010/0045489 A1 * | 2/2010 | Gondo | H03M 1/485 341/15 |
| 2012/0049889 A1 * | 3/2012 | Hatano | H10D 86/60 326/102 |
| 2015/0367077 A1 * | 12/2015 | Plambech | A61M 5/31528 604/211 |
| 2016/0008552 A1 | 1/2016 | Madsen et al. | |
| 2016/0287804 A1 | 10/2016 | Madsen et al. | |
| 2016/0287807 A1 | 10/2016 | Madsen et al. | |
| 2019/0022328 A1 | 1/2019 | Schleicher et al. | |
| 2021/0283339 A1 * | 9/2021 | Frazier | A61M 5/31585 |

FOREIGN PATENT DOCUMENTS

| | | | |
|---|---|---|---|
| EP | 4104884 A1 * | 12/2022 | ............... A61M 5/20 |
| JP | 2012-507314 A | 3/2012 | |
| JP | 2016-506845 A | 3/2016 | |
| WO | 9619872 | 6/1996 | |
| WO | 2014128157 A1 | 8/2014 | |
| WO | 16180873 | 11/2016 | |
| WO | 16193229 | 12/2016 | |
| WO | 17114768 | 7/2017 | |
| WO | 18013419 | 1/2018 | |
| WO | 18141571 | 8/2018 | |
| WO | 19040117 | 2/2019 | |
| WO | 19040313 | 2/2019 | |

OTHER PUBLICATIONS

Patent Cooperation Treaty International Search Report pertaining to International Application No. PCT/US2019/045895; Date of Mailing: Nov. 4, 2019.
Patent Cooperation Treaty Written Opinion of the International Searching Authority pertaining to International Application No. PCT/US2019/045895; Date of Mailing: Nov. 4, 2019.

* cited by examiner

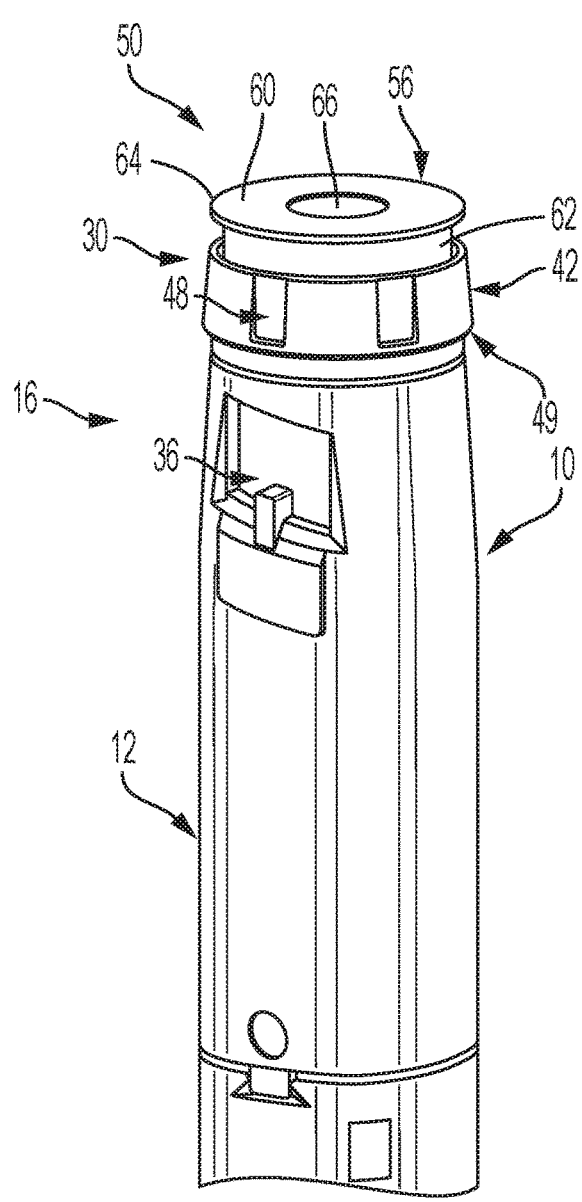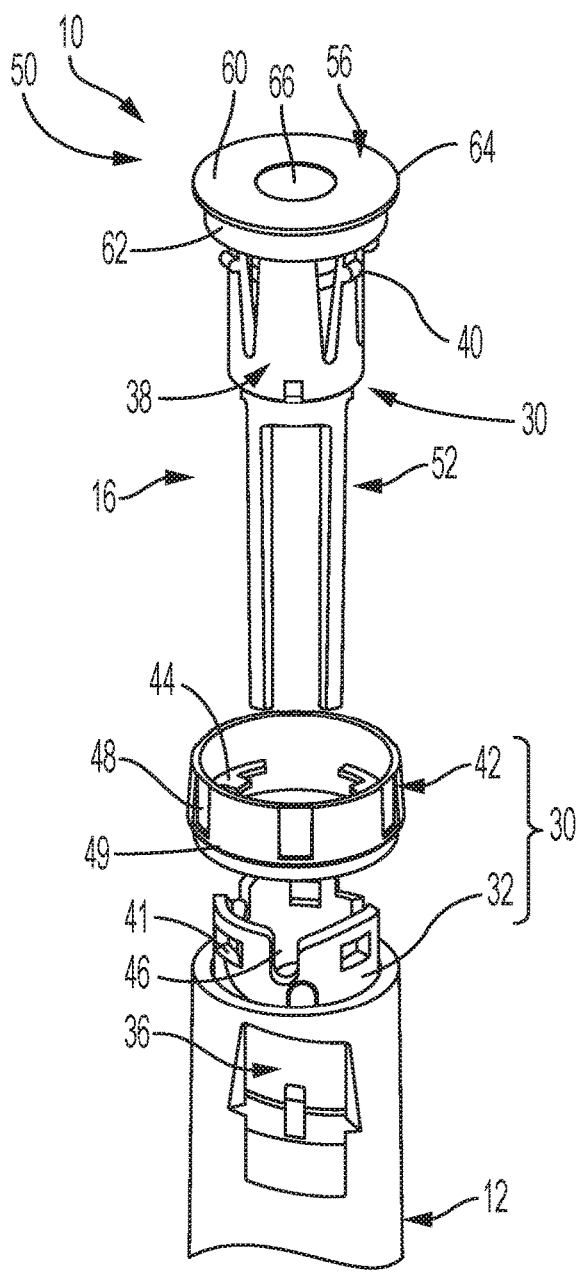
FIG. 3
FIG. 4

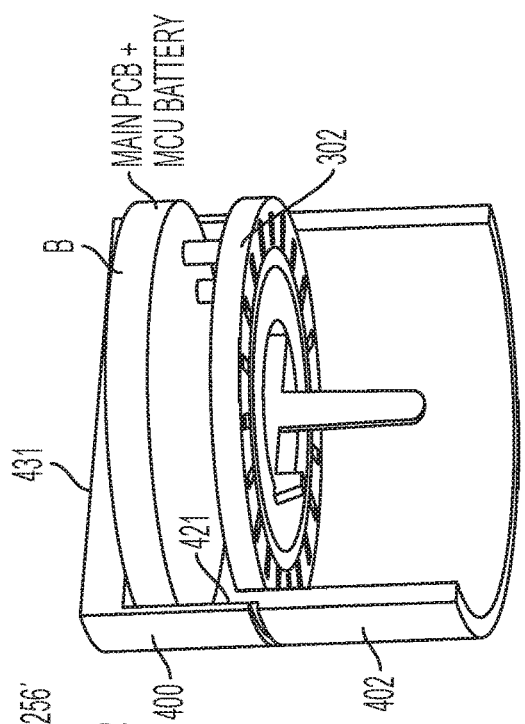
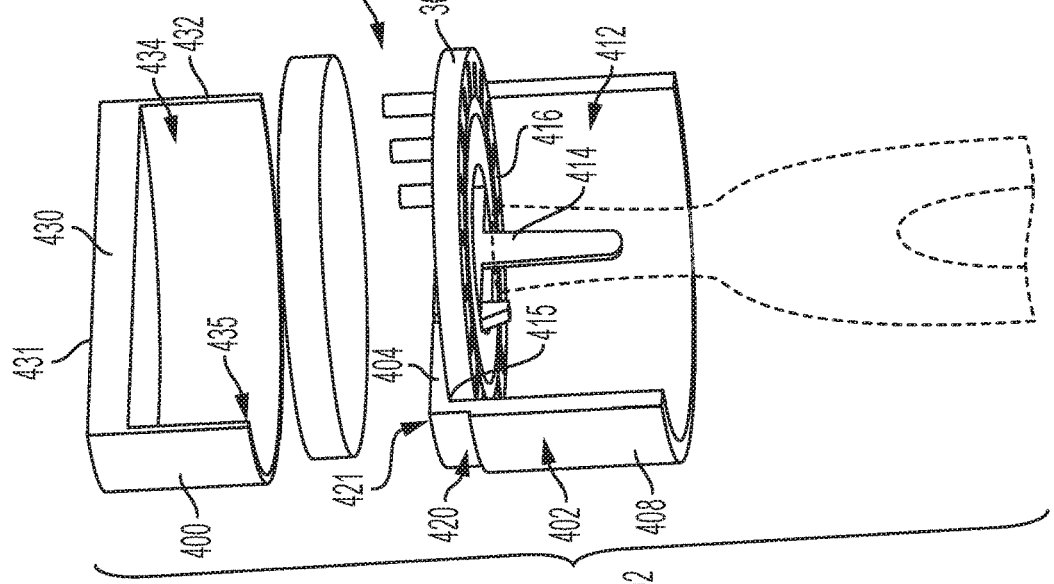
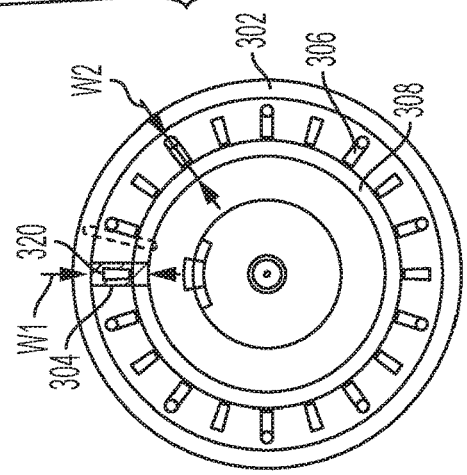
FIG. 10
FIG. 11
FIG. 12

MEDICATION DELIVERY DEVICE WITH DOSE DETECTION SYSTEM

TECHNICAL FIELD

The present disclosure relates to an electronic dose detection system for a medication delivery device, and illustratively to an electronic dose detection module or integrated dose detection system with contact sensing to detect data for determining a dose of medication delivered by the delivery device.

BACKGROUND

Patients suffering from various diseases must frequently inject themselves with medication. To allow a person to conveniently and accurately self-administer medicine, a variety of devices broadly known as injector or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many injector pens and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device and detects the relative movement of a sensed component secured to a second member of the device.

The administration of a proper amount of medication requires that the dose delivered by the medication delivery device be accurate. Many injector pens and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect information that can be correlated to the dose delivered by measuring mechanical parts which directly correspond to the dose displayed in the dose window to the user of the medication delivery device during an injection event. There is also a need to improve the accuracy and reliability of the detection system.

SUMMARY

In one embodiment, a delivery device includes a dose member rotatable during a dose dispensing event and a detection system that includes a position indicator, a position sensing member, a first electrical circuit and a second electrical circuit. One of the position indicator and the position sensing member is coupled to the dose member. The position sensing member includes a segmented radial pad and an electrically grounded radial pad disposed radially relative to one another along an axial surface of the position sensing member. The segmented radial pad includes a plurality of first segmented pads and a plurality of second segmented pads. The first and second segmented pads is disposed in an alternating pattern. The first electrical circuit is configured to generate a first signal in response to the position indicator being in a contacting relationship with the first segmented pads and the electrically grounded radial pad. The second electrical circuit is configured to generate a second signal in response to the position indicator is in a contacting relationship with the second segmented pads and the electrically grounded radial pad. A controller is in communication with the first and second electrical circuits, and is operable to determine a number of units of rotation of the dose member based on, directly or indirectly, at least one of the generated first and second signals.

In another embodiment, a method of determining an amount of dose dispensing with a delivery device is disclosed. The delivery device includes a position indicator and a position sensing member. One of the position indicator and the position sensing member is coupled to the dose member. The position sensing member includes a segmented radial pad and an electrically grounded radial pad disposed radially relative to one other along an axial surface of the position sensing member. The segmented radial pad includes a plurality of first segmented pads and a plurality of second segmented pads disposed in an alternating pattern. The position indicator is radially sized to contact the first segmented pads and the electrically grounded radial pad. The position indicator is radially sized to contact the second segmented pads and the electrically grounded radial pad. The first segmented pads are coupled to a first electrical circuit and the second segmented pads coupled to a second electrical circuit. At least one of the first and second electrical circuits coupled to a controller. The method including one or more of the following steps. Generating a first signal with the first electrical circuit when the position indicator is in contact with the electrically grounded radial pad and the first segmented pads. Generating a second signal with the second electrical circuit when the position indicator is in contact with the electrically grounded radial pad and the second segmented pads. Determining, with the controller, a number of units representative of an amount of rotation of the dose member based on at least one of the generated first and second signals.

BRIEF DESCRIPTION OF THE DRAWINGS

The features and advantages of the present disclosure will become more apparent to those skilled in the art upon consideration of the following detailed description taken in conjunction with the accompanying figures.

FIG. 3 is a perspective view of a proximal portion of the exemplary medication delivery device of FIG. 1.

FIG. 4 is a partially-exploded perspective view of the proximal portion of the exemplary medication delivery device of FIG. 3.

FIG. 10 is a schematic axial view of another embodiment of the dose detection system with a position indicator arranged over an electrical position sensing member.

FIG. 11 is a partially-exploded perspective view of a dose detection system arranged within a two-piece button.

FIG. 12 is a partial, perspective view of the dose detection system arranged within the two-piece button of FIG. 11 assembled.

DETAILED DESCRIPTION

Figure 1:
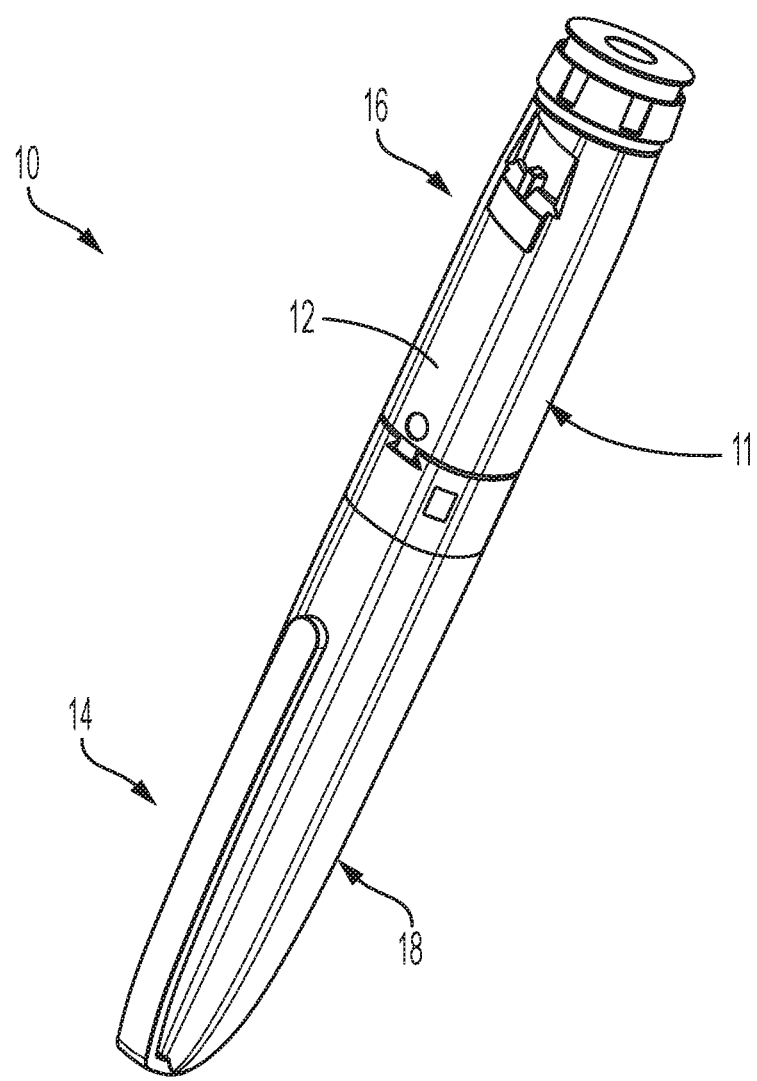
FIG. 1 is a perspective view of an exemplary medication delivery device of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is configured for sensing of relative rotational movement between a dose setting member and an actuator of the medication delivery device in order to determine the amount of a dose delivered by a medication delivery device. Such amount of dose delivered may then be indicated and/or communicated to the patient or healthcare provider, such as, for example, on a LED display of the device, with a medical mobile app of a mobile phone, a computer via a website, or any combination thereof. In some embodiments, the device is configured to determine the units of rotation which is then communicated to an external device that correlates the total units of rotation with an amount of dose. In other words, the sensed relative rotational movements are correlated to the amount of the dose delivered.

By way of illustration, the medication delivery device is described in the form of a pen injector. However, the medication delivery device may be any device which is used to set and to deliver a dose of a medication, such as, for example, pen injectors, infusion pumps and syringes, bolus injectors, and/or autoinjectors. The medication may be any of a type that may be delivered by such a medication delivery device. In one example, the delivery device includes a dose member rotatable during a dose dispensing event and a dose detection system for determining the start and end of rotation of the dose member, and the total amount of rotational movement, which can be utilized for determining the total amount of dose delivered. In one example, the dose detection system includes a position indicator and a position sensing member. The position sensing member may include a segmented radial pad and an electrically grounded radial pad disposed radially relative to one other along an axial surface of the position sensing member. The segmented radial pad may include a plurality of first and second segmented pads disposed relative to each other in an alternating pattern. The position indicator may be sized or shaped to be in contact with the first segmented pads and the electrically grounded radial pad for a first electrical circuit to generate a first signal, and in contact with the second segmented pads and the electrically grounded radial pad for a second electrical circuit to generate a second signal. Such detection systems described herein may provide improved accuracy and reliability of determining the amount of rotation over other sliding contact systems that are arranged with contact event counters or other means, which are susceptible to signals with higher than desirable noise, such as signal debounce; thus, susceptible to variable frequency during dosing; susceptible to contact with pads sustained longer than debounce time; and/or susceptible to repeat count if contact arm touches same pad on subsequent dose.

The delivery device may have a control system integrated within the device body. In one example, the control system is located primarily within the button. In other embodiments, the control system is integrated within a separate modular unit attachable to the button of the device. The control system may include a controller to receive the signals and determine the amount of rotation during dose dispensing and/or dose setting. The control system may have a communication module configured to wirelessly transmit data of the amount of rotation or determined dose amount to an external device. In some embodiments, the control system includes a latch circuit and/or event log module to reduce processing power demand of the controller. In some embodiments, the control system may determine the amount of rotation from two signals with software instruction programmed within the processing core and memory of the controller.

Devices described herein, such as a device 10, 210, or 700, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

An exemplary medication delivery device 10 is illustrated in FIGS. 1-4 as an injector pen configured to inject a medication into a patient through a needle 24. Although the illustrative medication delivery device 10 is an injector pen, the medication delivery device 10 may be any device which is used to set and to deliver a dose of a medication. The medication may be of any type that may be delivered by such a medication delivery device 10.

Figure 2:
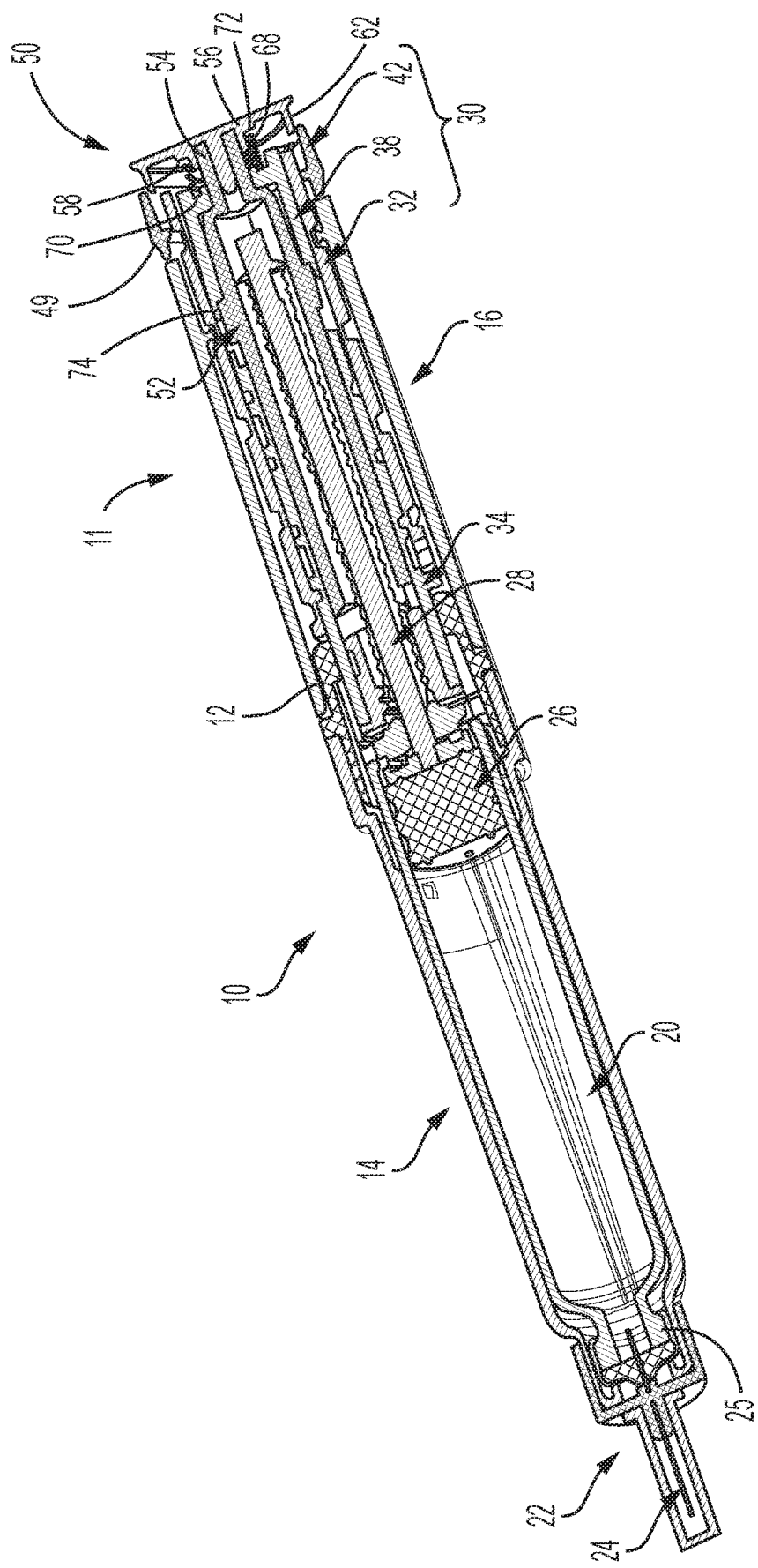
FIG. 2 is a cross-sectional perspective longitudinal view of the exemplary medication delivery device of FIG. 1.

Medication delivery device 10 includes a body 11 shaped in a manner of the kind of device having a distal portion 14 and a proximal portion 16. For the illustrated device 10, the body 11 includes an elongated, pen-shaped housing 12 including the distal portion 14 and the proximal portion 16 arranged along a longitudinal axis L. Distal portion 14 is receivable within a pen cap 18. Referring to FIG. 2, distal portion 14 contains a reservoir or cartridge 20 configured to hold the medicinal fluid to be dispensed through its distal outlet end 25 during a dispensing operation. In other embodiments, the distal portion 14 is configured to receive a cartridge that is replaceable such as in a reusable device. The outlet end 25 of distal portion 14 is equipped with a removable needle assembly 22 including an injection needle 24. A piston 26 is positioned in fluid reservoir 20. An injecting mechanism or drive member 28, illustratively a screw, is positioned in proximal portion 16 and is axially moveable relative to housing 12 along longitudinal axis L to advance piston 26 toward the outlet end 25 of reservoir 20 during the dose dispensing operation to force the contained medicine through the needled outlet end 25.

A dose setting member 30 is coupled to housing 12 for setting a dose amount to be dispensed by device 10. In the illustrated embodiment, dose setting member 30 is in the form of a screw element operative to spiral (i.e., simultaneously move axially along longitudinal axis L and rotationally about longitudinal axis L) relative to housing 12 during dose setting and dose dispensing operations. FIGS. 1 and 2 illustrate the dose setting member 30 fully screwed into housing 12 at its home or zero position. Dose setting member 30 is operative to screw out from housing 12 in a proximal direction until it reaches an extended position corresponding a desired dose setting. The extended positon may be any position between a position corresponding to an incremental extended position (such as a dose setting a 0.5 or 1 unit) to a fully extended position corresponding to a maximum dose deliverable by device 10 in a single injection and to screw into housing 12 in a distal direction until it reaches the home or zero position corresponding to a minimum dose deliverable by device 10 in a single injection.

Referring to FIGS. 2-4, dose setting member 30 may include a cylindrical dial member 32 having a helically threaded outer surface 33 that engages a corresponding threaded inner surface 13 of housing 12 to allow dose setting member 30 to spiral relative to housing 12. Dial member 32 may include a helically threaded inner surface that engages a threaded outer surface of sleeve 34 (FIG. 2) of device 10.

The outer surface 33 of dial member 32 may include dose indicator markings, such as numbers that are visible through a dosage window 36 to indicate to the user the set dose amount. Dose setting member 30 is shown further including a tubular flange 38 that is coupled in the open proximal end of dial member 32 and is axially and rotationally locked to dial member 32 by detents 40 received within openings 41 in dial member 32. Dose setting member 30 may further includes a skirt or collar 42 positioned around the outer periphery of dial member 32 at its proximal end. Skirt 42 is axially and rotationally locked to dial member 32 by tabs 44 received in slots 46.

The dose setting member 30 therefore may be considered to comprise any or all of dial member 32, flange 38, and skirt 42, as they are all rotationally and axially fixed together. The dial member 32 is directly involved in setting the dose and driving delivery of the medication. The flange 38 is attached to the dial member 32 and, as described later, cooperates with a clutch 52 to selectively couple the dial member 32 with a dose button 56. Skirt 42 provides a surface external of body 11 to rotate the dial member 32.

In the embodiment illustrated in FIG. 1, the dose button 56 of the illustrated device 10 is a one-piece component which combines both skirt 42 and the dose button 56 of FIG. 1-4. In this embodiment, the flange 38 is attached to the dial member 32 and cooperates with a clutch 52 to selectively couple the dial member 32 with the one-piece dose button 56. The radial exterior surface of one-piece dose button 56 provides a surface external of body 11 to rotate the dial member 32.

Skirt 42 illustratively includes a plurality of surface features 48 formed on the outer surface 49 of skirt 42. Surface features 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose button 56 and/or dial member 32 for dose setting. A user may grasp and rotate the radial exterior surface of button 56, which also includes a plurality of surface features, for dose setting.

Figure 5:
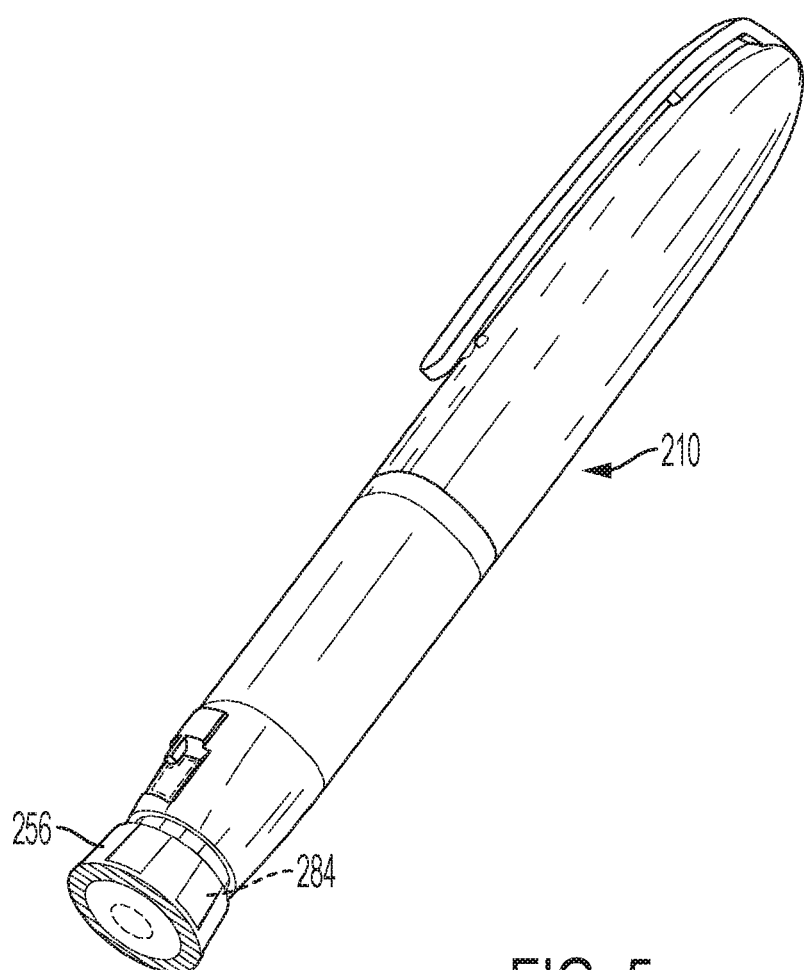
FIG. 5 is a perspective view of another exemplary medication delivery device of the present disclosure with a button.
Figure 6:
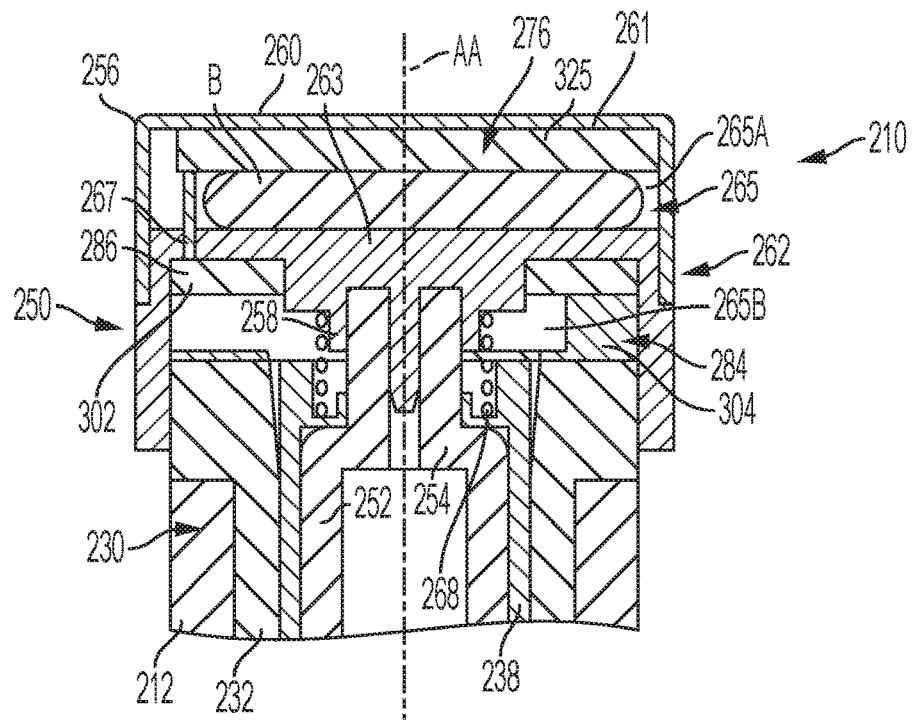
FIG. 6 is a cross-sectional view of a dose detection system according to an exemplary embodiment disposed within the proximal portion of the medication delivery device of FIG. 5.

Referring to FIGS. 3-4, delivery device 10 includes an actuator 50 having clutch 52 which is received within dial member 32. Clutch 52 includes an axially extending stem 54 at its proximal end, such as shown in FIG. 2. Actuator 50 further includes a dose button 56 positioned proximally of skirt 42 of dose setting member 30. Actuator 50 may also comprise a button configured without the skirt, referred to as button 256, as shown in FIGS. 5-6. Dose button 56 in FIG. 2 includes a mounting collar 58 centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inwardly of the outer peripheral edge of face 60 to form an annular lip 64 there between. Proximal face 60 of dose button 56 serves as a push surface against which a force can be applied manually, i.e., directly by the user to push actuator 50 in a distal direction. Dose button 56 illustratively includes a recessed portion 66 centrally located on proximal face 60 (FIGS. 3 and 4), although proximal face 60 alternatively may be a flat surface. Similarly, dose button 256 shown in FIG. 5 including the recessed portion centrally located on proximal face or alternatively may be a flat surface. A bias member 68, illustratively a spring, is disposed between the distal surface 72 of button 56 and a proximal surface 70 of tubular flange 38 to urge actuator 50 and dose setting member 30 axially away from each other. Dose button 56 is depressible by a user to initiate the dose dispensing operation.

Delivery device 10 is operable in a dose setting mode of operation and a dose dispensing or delivery mode of operation, as described further below. In the embodiment shown in FIG. 5, dose button 256 behaves substantially the same as dose button 56 in the description below. Cap is removed to expose the needle of a prefilled syringe system or a needle hub in case of a cartridge based system. Needle protector is also removed such that the needle is fully exposed and ready for drug administration.

In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" equals one unit or one-half unit of medication. The set dose amount is visible to the user via the dial indicator markings shown through dosage window 36. Actuator 50, including button 56 and clutch 52, move axially and rotationally with dose setting member 30 during the dialing of the dose setting mode, because dose button 56 of actuator 50 is rotationally fixed relative to skirt 42 of dose setting member 30 by complementary and mutually-facing splines 74 (FIG. 2) urged together by bias member 68. In the course of the dose setting operation, skirt 42 and dose button 56 move relative to housing 12 in a spiral manner from a "start" position to an "end" position. This rotation relative to the housing 12 is proportional to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56 along longitudinal axis L. This axial distal force causes axial movement of actuator 50 in the distal direction relative to housing 12 along longitudinal axis L. The axial force may be applied by the user directly or indirectly to dose button 56, as described further below. The dose dispensing mode of operation may also be initiated by activating a separate switch or trigger mechanism.

The axial shifting motion of actuator 50 compresses biasing member 68 and reduces or closes the gap between dose button 56 and tubular flange 38. This relative axial movement separates complementary splines 74 (FIG. 2) on the clutch 52 and flange 38, and thereby disengages actuator 50 from being rotationally fixed to dose setting member 30. In particular, dose setting member 30 is rotationally uncoupled from actuator 50 to allow back-driving rotation of dose setting member 30 relative to actuator 50.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device 10 is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3. Device 10 may needed primed prior to delivery of a desired amount of medication for treatment. For example, a prime shot of 1 to 2 units of drug through the needle may be undertaken prior to resetting the dose dial for the desired amount of medication to be delivered for treatment.

The above-described "start" and "end" angular positions of dose dial member 32, and therefore of the rotationally fixed flange 38 and skirt 42, of the dose setting member 30 relative to dose button 56 of actuator 50 provide an "absolute" change in angular positions during the dose dispensing operation. Determining the degree of relative rotation is determined in a number of ways. By way of example, total rotation may be determined by also taking into account the incremental movements of the dose setting member 30 which measured in any number of ways by a detection sensor system, such as described below.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein. Another example of the delivery device is an auto-injector device that may be found in U.S. Pat. No. 8,734,394, entitled "Automatic Injection Device With Delay Mechanism Including Dual Functioning Biasing Member," which is hereby incorporated by reference in its entirety, where such device being modified with one or more various sensor systems described herein to determine an amount of medication delivered from the medication delivery device based on the sensing of relative rotation within the medication delivery device. Another example of the delivery device is a reusable pen device that may be found in U.S. Pat. No. 7,195,616, entitled "Medication Injector Apparatus with Drive Assembly that Facilitates Reset," which is hereby incorporated by reference in its entirety, where such device being modified with one or more various sensor systems described herein to determine an amount of medication delivered from the medication delivery device based on the sensing of relative rotation within the medication delivery device.

FIG. 5 illustrates another embodiment of the device, now referenced as 210, with a detection sensor system 284 (dashed line to denote it is within the device and button) disposed within the dose button 256 without the skirt 42. Although not shown, detection sensor system 284 may be incorporated in the device 10. FIG. 6 illustrates a cross-sectional view of the proximal portion of the device 210. The device 210 includes many of the same components that are operational for dose setting and dose dispensing as described with reference to the device 10, including at least a portion of the electronic components in the electronics assembly, and such components will have the same corresponding descriptions. Although the device 210 is shown as a device within an integrated dose detection sensing system, such sensing system may be incorporated in a module for removable attachment to a dose button. Also, the dose detection system 284 may be provided with the button configuration with the skirt 42 shown in FIGS. 1-4.

The dose detection system 284 is disclosed for use with medication delivery device of the present disclosure or another suitable medication delivery device. Dose detection system 284 may sense rotation of the dose setting member relative to actuator and/or another component of medication delivery device during the dose dispensing operation. The sensed rotation of the dose setting member, such as the start and end positions and/or total movement, may be used to determine the amount of medication delivered from medication delivery device. Dose detection system 284 may be a modular component that is removably coupled to the medication delivery device. This removable coupling allows dose detection system 284 to be removed from a first medication delivery device and thereafter attached to a second medication delivery device.

The dose setting member 230 is coupled to the device housing 212 for setting a dose amount to be dispensed by device 210. Dose setting member 230 is operative to screw out in a proximal direction from housing 212 until it reaches any position up to and including a fully extended position corresponding to a maximum dose deliverable by device 210 in a single injection. The cylindrical dose dial member 232 of dose setting member 230 includes the helically threaded outer surface that engages the corresponding threaded inner surface of housing 212 to allow dose setting member 230 to spiral relative to housing 212. Dose dial member 232 includes the helically threaded inner surface that engages the threaded outer surface of the sleeve of the device 210, such as sleeve 34 in FIG. 2. The outer surface of dial member 232 may include dose indicator markings that are visible through the dosage window to indicate to the user the set dose amount. Tubular flange 238 of dose setting member 230 is illustrated coupled in the open proximal end of dial member 232 and is axially and rotationally locked to dose dial member 232 by detents received within openings in dial member 232, such as, for example, shown in FIG. 2.

The actuator 250 of delivery device 210 is shown including the clutch 252 that is received within dose dial member 232. The proximal end of the clutch 252 includes the stem 254 that is axially extending from its proximal end. Dose button 256 of actuator 250 is positioned proximally of dose setting member 230, as shown. The mounting collar 258 of dose button 256 is attached to stem 254 of clutch 252, such as with an interference fit or an ultrasonic weld, so as to axially and rotatably fix together dose button 256 and clutch 252. The bias member 268, illustratively a spring, is disposed between the distal surface of mounting collar 258 and the proximal surface of tubular flange 238 to urge actuator 250 and dose setting member 230 axially away from each other. Dose button 256 is depressible by a user to initiate the dose dispensing operation. Bias member 268 biases the dose button 256 in the proximal first position (as shown in FIG. 6) where it stays during dose setting operation, until the user applies an axial force great enough to overcome the biasing force of member 268 to move the dose button 256 to the distal second position for dose dispensing operation.

Dose button 256 includes an upper proximal wall 261 with the disk-shaped proximal end surface 260 and the annular wall portion 262 extending distally from the proximal wall 261 to define a button housing cavity 265. Surface 260 of dose button 256 serves as the push surface against which a force can be applied manually, i.e., directly by the user to push actuator 250 in a distal direction. Dose button 256 include a distal wall 263 axially spaced from the proximal wall 261. Distal wall 263 may at least partially divide the cavity 265 into two proximal upper and distal lower cavity portions 265A, 265B, respectively. The mounting collar 258 of dose button 256 is shown extending distally from an intermediate location of the distal wall 263 for attachment with stem 254 of clutch 252.

Distal wall 263 may be configured to allow a portion, such as connector or electrical conduits, of the sensor system to extend axially beyond the distal wall 263. Distal wall 263 may include a discrete opening 267 or may extend partially across the cavity 265 from a portion of the annular wall portion 262 to stop short of the opposite end of annular wall portion to define an axial aperture. The opening 267 or aperture may be spaced radially from the axis AA toward the outer end.

The control system of the detection sensor system 284 includes an electronics assembly 276 shown housed within the dose button 256. The circuit board 325 of electronics assembly 276 includes a plurality of electronic components, and is shown mounted on the distal face of the proximal wall 261. The detection sensor system 284 includes the rotational sensor 286 operatively communicating with the controller of the circuit board 325 for receiving signals from the sensors representative of the sensed rotation. The rotational sensor 286 may be mounted to a distal face of the circuit board 325. In one embodiment, the rotational sensor 286 includes an electrical position sensing member 302 shown electrically connected to circuit board 325 via a conduit or lead extending through opening 267 and a position indicator 304. The controller of the electronics assembly 276, such as, for example, shown in FIG. 13, includes at least one processing core in electric communication and internal memory. The control system of the detection sensor system 284 includes a battery B, illustratively a coin cell battery, as a power source for powering the electronics components. The processing core of the controller includes control logic operative to perform the operations described herein, including detecting a dose delivered by the medication delivery device based on a detected rotation of the dose setting member relative to the actuator. The components in the electronics assembly are shown as unconnected for illustrative purposes only, and are actually electrically connected to one another as understood in the art.

Various sensor systems are contemplated herein. In general, the detection sensor system comprises at least a pair of sensing components-a sensing component and a sensed component. The term "sensing component" refers to any component which is able to detect the relative angular position or movement of a sensed element. The sensing component includes a sensor along with associated electrical components to operate the sensor. The "sensed element" is any component which moves relative to the associated sensor and for which the sensor is able to detect movement relative to the sensor. The sensed component comprises one or more sensed elements. Thus, the sensor is able to detect the movement of the sensed element(s) and to provide outputs representative of the relative position(s) of the sensed element.

Figure 7:
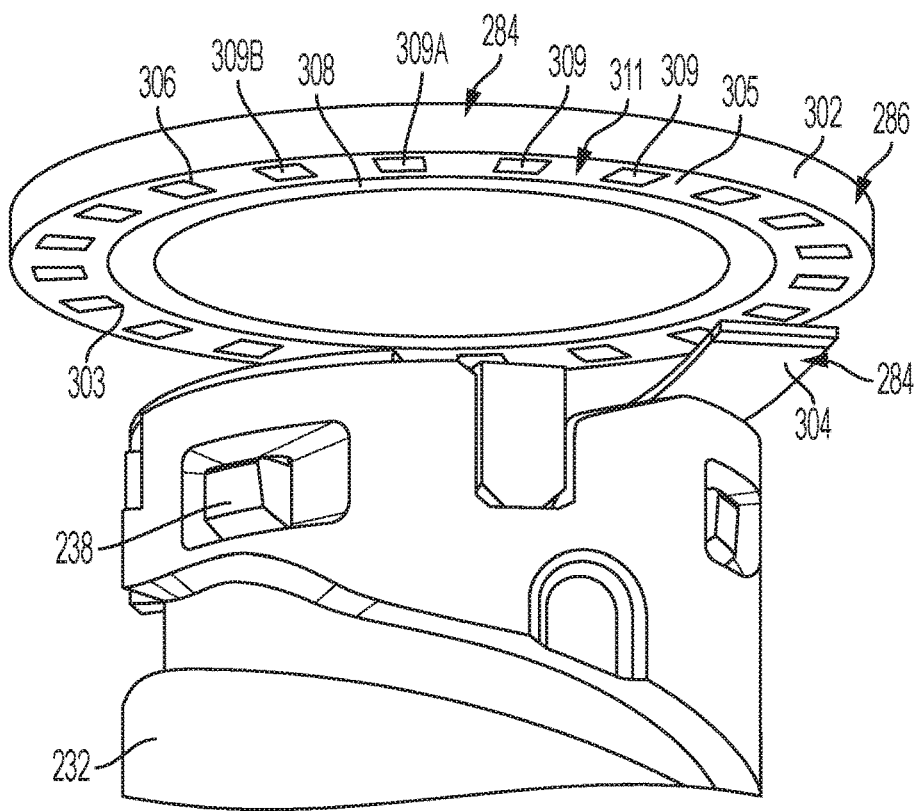
FIG. 7 is a partially-exploded perspective view of the dose detection system of FIG. 6.

The detection sensor system 284 is shown in more detail in FIG. 7. The rotational sensor 286 of detection sensor system 284 includes the electrical position sensing member 302, as the sensing component, and the position indicator 304, as the sensed component, which is engageable with the electrical position sensing member 302. When the dose button 256 is at its proximal first position for dose setting operation, the sensing member 302 is axially spaced from engagement with the position indicator 304. When the dose button 256 is moved to its distal second position for dose dispensing operation, the sensing member 302 is axially moved to engage with the position indicator 304. Alternatively, the position indicator may maintain engagement with the sensing member during dose setting and dose dispensing. The position indicator 304 is configured to electrically contact with the electrical position sensing member 302 during the dose dispensing operation and generate a signal indicative of an incremental movement of the position indicator 304 along the electrical position sensing member 302.

Electrical position sensing member 302 may have a disc shape or annular shape formed at least partially circuit board material. One or more electrical contact sensing pads 303 may be disposed along a needle facing side 305 of the sensing member 302. In one embodiment, the contact pad may include a single ring (not shown). In another embodiment, a pair of contact pads 303 includes a first ring 306 and a second ring 308 disposed radially inward from the first ring 306 in a concentric arrangement. One of the first and second rings may be a continuous ring, and the other of the first and second rings may be a segmented ring, that is, including a plurality of arcuate ring segments disposed circumferentially from one another by a gap therebetween. The number of ring segments and gap distance between the pad segments may be provided to provide electrical signals to determine the desired incremental positon of the dose member. In another example, both of the rings may be segmented, including a plurality of arcuate ring segments disposed circumferentially from one another by a gap therebetween, with one of the rings being electrically grounded and the other for contacting to generate a signal.

Figure 8:
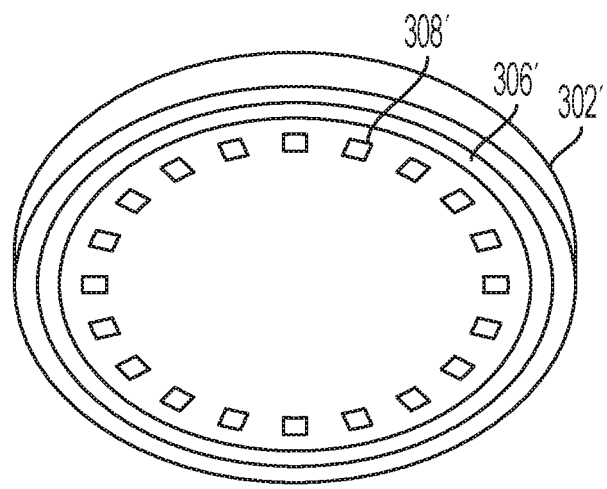
FIG. 8 is a perspective view of another embodiment of an electrical position sensing member of the dose detection system of FIG. 6.
Figure 16:
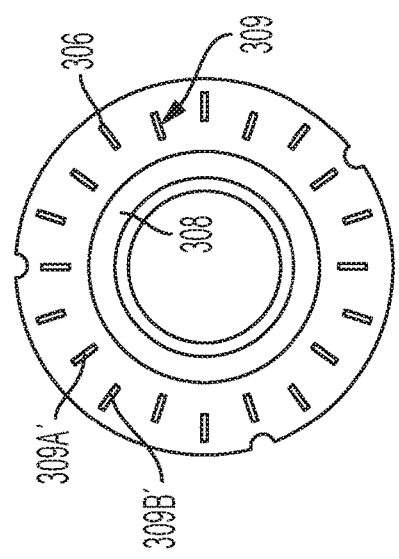
FIG. 16 is an axial view of another embodiment of an electrical position sensing member for any of the dose detection systems described herein.

In one embodiment, the second ring 308 is the continuous one and the first ring 306 is the segmented ring, as shown in FIG. 7. Here, the first ring 306 includes a plurality of arcuate ring segments 309 disposed circumferentially from one another by a gap region of non-sensing material, referred to as numeral 311, which are arranged to form a ring shape. The number of segments 309 may be in a range of 10 to 36; and in one example, 20 segments are provided. In one form, one set of segment pads 309, such as, for example, half the number of pads, are coupled to a first circuit, such as a set circuit, and one set of segment pads 309, such as, for example, half the number of pads, are coupled a second circuit, such as a reset circuit. The pads with the different circuits are in an alternating pattern with one another, such as described later. In another embodiment of the electrical position sensing member, referred to as 302', the first ring 306' is the continuous one and the second ring 308' is the segmented ring, as shown in FIG. 8. One of the first and second rings may be configured as electrically grounded, and the other of the first and second rings may be configured as the sensing portion electrically coupled to the controller. In one embodiment shown, the second ring 308 that is continuous is electrically grounded, and the first ring 306 that is segmented is used for generating the sensing signal. FIG. 7 depicts the pads 309 disposed from the longitudinal axis at an equal radius. FIG. 16 depicts the electrical position sensing member including the inner ring 308 as the continuous ground ring and the outer ring 306 as the segmented ring of pads 309 in an alternating arrangement and that are coupled to the first and second circuits, respectively. The pads 309 in FIG. 16 are radially offset from one another, that is, the pads 309A' coupled to the first circuit are disposed radially inward from the adjacent pads 309B' which are coupled to the second circuit, or vice versa. In one embodiment, the second ring 309 comprises a second ring of pad segments 309A or 309A' electrically connected to the first circuit and a third ring of pad segments 309B or 309B' electrically connected to the second circuit. The pad segments 309A or 309A' may be spaced radially from the axis by a common radial distance. The pad segments 309B or 309B' may be spaced radially from the axis by a common radial distance. In one example, the pad segments 309B or 309B' are circumferentially offset relative to the respective pad segments 309A or 309A' such that the pad segments define an alternating pattern. The second ring of pad segments 309A or 309A' and the third ring of pad segments 309B or 309B' may be spaced radially from the axis at approximately the same radial distance, as shown in FIG. 7, or at different radial distances, as shown in FIG. 16.

Figure 9:
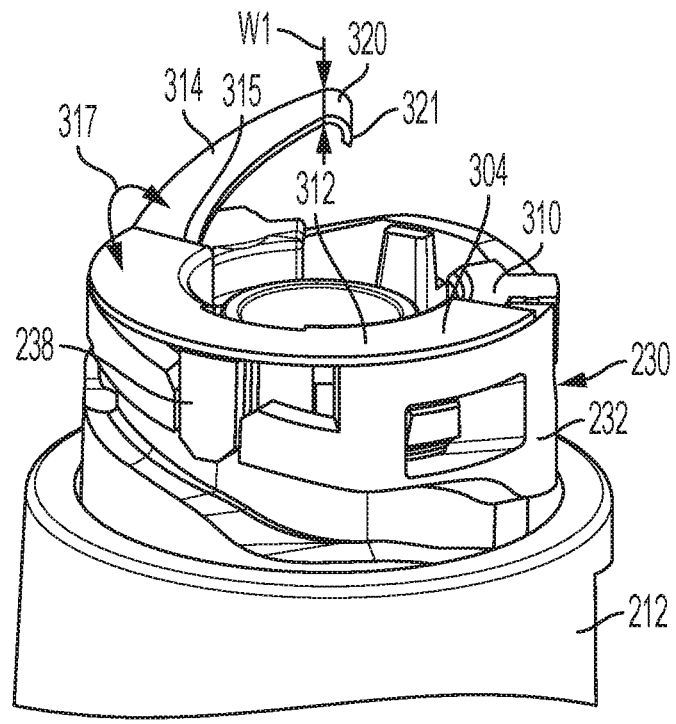
FIG. 9 is a partially-exploded perspective view of the dose detection system of FIG. 6, with the electrical position sensing member omitted.
Figure 22:
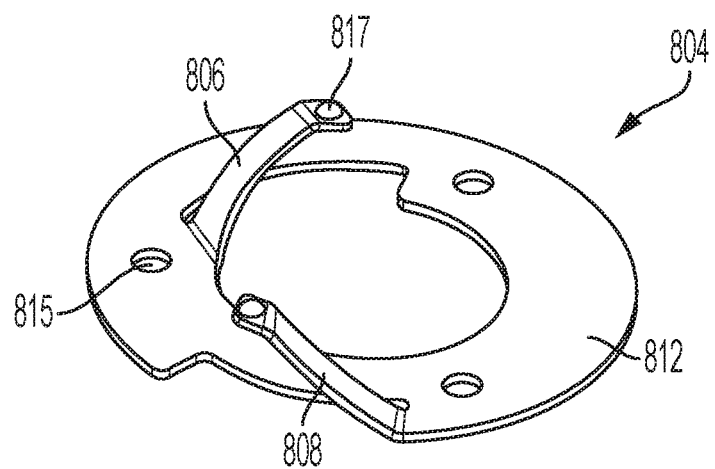
FIG. 22 depicts another embodiment of a position indicator for any of the dose detection systems described herein.

In FIG. 9, position indicator 304 is shown coupled to the dose setting member 230 in a rotationally and axially fixed manner. In one embodiment, the position indicator 304 is coupled to the button facing surface 310 of the flange 238. Position indicator 304 may include a base 312 configured to couple to the dose setting member 230, such as the flange described above, and one or more indicator arms 314 extending proximally from the base 312. The base 312 may have an arcuate shape, and is shown having a semi-ring configuration, although a full ring shape may be employed, such as shown in FIG. 22. Base 312 may be fixedly coupled to the proximal axial surface of the dose setting member component, such as, for example, the flange, such as, for example, by having mounting holes, such as shown in FIG. 22, for receiving staking posts and ultrasonic welding. Other attachment mechanism may be used such as adhesives or friction fit. The position indicator 304 is configured to contact a portion of the rings 306, 308 at the same time. Indicator arm 314 may extend from one of the circumferential ends 315 of the base 312 at an obtuse angle 317 relative to the base plane, although the angle 317 of extension of the arm 314 may be orthogonal or acute relative to the base. In one example, any part of the arm 314 includes a contacting portion contactable with both of the pads 303 simultaneously. The tip end 320 of the indicator arm 314 may be configured to contact one or more of the electrical contact pads 303. In one embodiment, the tip end 320 has a radial width W1 sized to contact both of the first and second rings 306, 308 at the same time. FIG. 10 illustrates the radial width W1 of the tip end 320 and the combined radial width W2 of the first and second rings 306, 308. Radial width W1 may be sized to 50% to 150% of the combined radial width W2. In another example described later, more than one arm with a contacting portion may be employed to contact the respective rings simultaneously.

Figure 23:
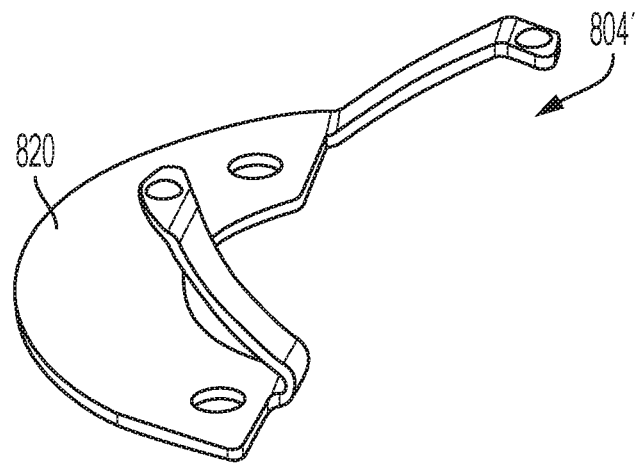
FIG. 23 depicts another embodiment of a position indicator for any of the dose detection systems described herein.

Referring to FIG. 9 and FIGS. 20 and 22-23, the tip end of the arm may be configured for enhanced sliding contact along and between the pads 303, including having a polished or smoothed surface and/or a rounded surface (as shown by the hook shape 321) and/or a domed surface (such as shown in FIGS. 22-23) to avoid potential snags during its travel. The indicator arms described herein may be resilient, being biased at a particular axial location from its base. For example, the indicator arm may have a natural configuration when the indicator arm is axially spaced from the base at a maximum extent, as shown, for example, in FIG. 9. Any contact with the electrical position sensing member may move the indicator arm from its natural state, and, due to the resiliency of the arm, the arm may apply an axial force as the tip end engages the contact pads of the sensing member. Such axial force may ensure that the tip end of the position indicator remains engaged with the contact pads during sensing to inhibit sensing errors. The base and indicator arm of the position indicators described herein may be formed integrally from the same material, such as, an electrically conductive material, such as metal. The base and indicator arm may be formed separately from same materials or different materials. If formed separately, the base and indicator arm may be coupled to one another, such as, for example, welding, metal welding epoxy, brazing, or other means depending on the materials of the components. The base and indicator arm may be formed from a plastic material having conductive material impregnating the plastic material in at least the tip end portion or having a conductive material coating along the tip end. In one example, the base and indicator arm is formed integrally from an electrically conductive metallic material and are coupled to one another at a living hinge joint such that the indicator has a leaf spring configuration.

Figure 13:
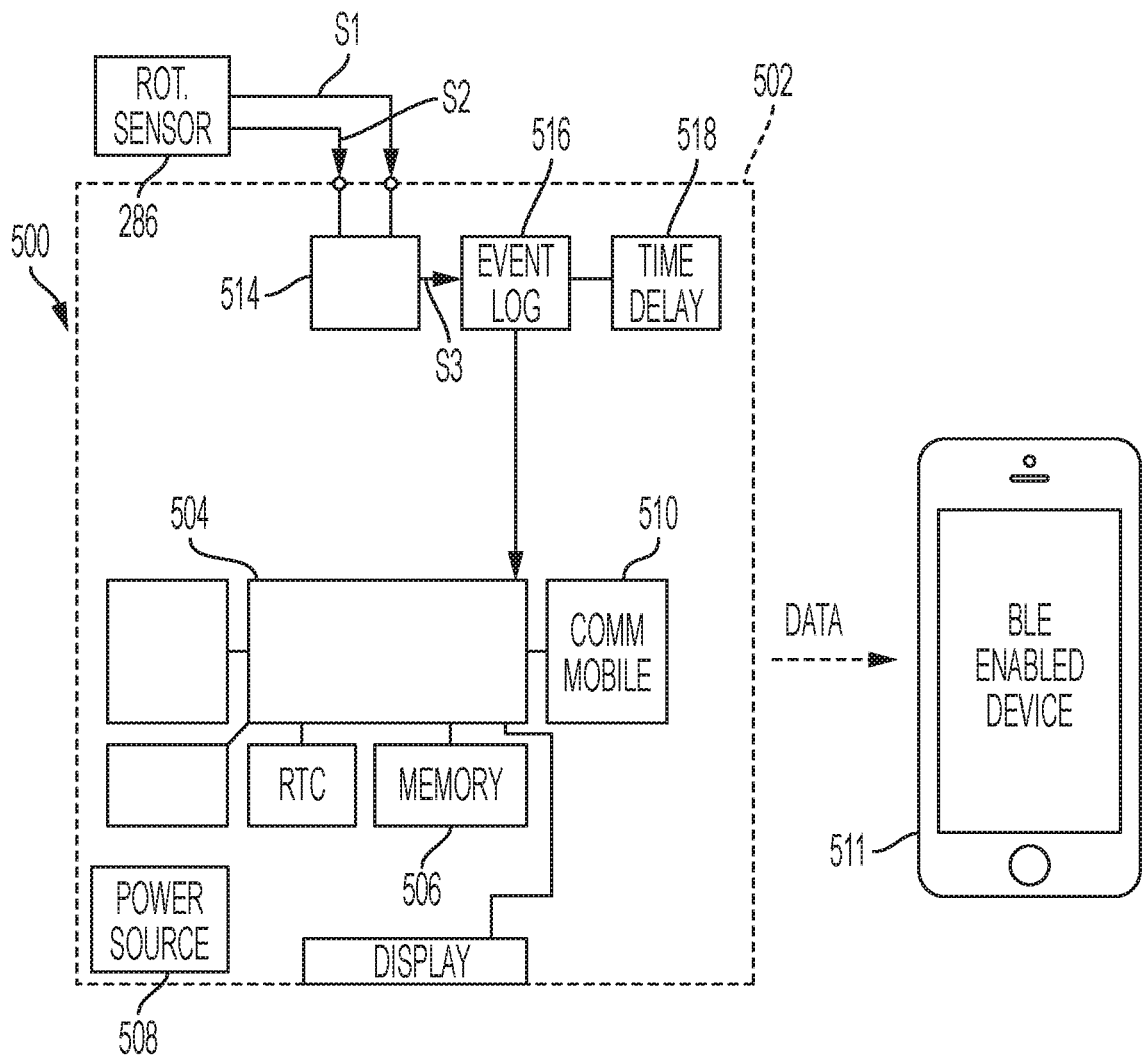
FIG. 13 is a schematic of the dose detection system in communication with a control system that is in communication with a paired external device.

During dose dispensing, the position indicator 304 rotates relative to the electrical position sensing member 302 which does not rotate during dose dispensing. Position indicator 304 is configured to contact the contact pads 303, that is the first and second rings 306, 308 of electrical position sensing member simultaneously during dose dispensing to generate electrical signals that are sent to the controller. For example, when the tip end 320 of the indicator arm, or of indicator arms in some embodiments, is in electrical contact with the first ring 306 and the second ring 308, such as, for example, the continuous pad and the first and second segmented sensing pads, an electrical signal is generated. When the position indicator 304 rotates relative to the stationary electrical position sensing member 302 such that the tip end 320 of the indicator arm 304 is disposed along the gap region 311 between segments 309 of one of the rings and in contact with the other ring, the previously generated electrical signal will stop. The controller, such as, for example, shown in FIG. 13, is configured to determine a dose count from the generated signals. From the determined dose counts, the controller may communicate the dose record including the initial dose count and the final dose count or the total number of dose counts to an external device for determining the total angular movement of the dose setting member and thus the correlated total amount of dose dispensing. In one example, the initial count will the final count from the previous dose. The controller may also be configured to determine the total number of dose counts and correlate the number count with the total angular movement of the dose setting member, with a look up table or database stored in memory, and thus the determine the total amount of dose dispensed to generate the dose record. The determined dose may be indicated on a LED display, such as, for example, indicated in FIG. 13, along the device and/or communicated to the external device for indication to the user.

FIGS. 11-12 illustrate an embodiment of a two-piece button housing configured to retain the detection sensor system 284. The button, referred to as 256', includes an upper proximal housing portion 400 and a lower distal housing portion 402. The lower distal portion 402 includes an axial wall 404 and a radial wall 408 extending distally from the axial wall 404 to form an inverted cup shape. The walls 404, 408 together define a lower distal portion cavity 412 that is sized and shaped to receive the electrical position sensing member 302. The mounting collar 414 of dose button 256' extends from the needle facing surface 415 of the axial wall 404 for attachment to the stem of the clutch, so as to axially and rotatably fix together dose button 256' and the clutch. The electrical position sensing member 302 is shaped with a central bore 416 that is sized to fit circumferentially around the mounting collar. During assembly, the electrical position sensing member 302 is inserted within the cavity 412 and placed against the surface 415 of the axial wall 404, which may be free floating or affixed to the surface or to the walls. An annular recess 420 may be formed along the upper proximal end of the radial wall 408. The recess 420 defines a recessed proximal region 421 that is sized to receive the lower distal end of the proximal portion 400. Although not shown in FIGS. 11-12, the opening (similar to opening 267) is formed to allow the passage of connector and/or conduits for communication with the controller.

The upper proximal portion 400 includes an axial wall 430 and a radial wall 432 extending distally from the axial wall 430 to form an inverted cup shape. The walls 430, 432 together define an upper proximal portion cavity 434 that is sized and shaped to receive the circuit board 325 and/or battery B and/or other components. The axial wall 430 includes a proximal or upper surface 431 that faces the user and a distal or lower surface 433 that faces the lower housing 402. The operator may deliver a dose by applying an axial distal force along longitudinal axis AA (FIG. 6) to upper surface 431. This axial distal force may be transferred from proximal portion 400 to lower housing 402 of dose button 256'. The rest of the dose dispensing operation may continue as described. In one embodiment, the lower distal end 435 of the proximal portion 400 is sized to fit over the recessed proximal region 421 of the lower distal portion 420, as shown in FIG. 12. In another embodiment (not shown), cavity 434 of the proximal portion 400 is sized to receive the lower distal portion 402 such that the radial wall 432 extends over the radial wall 408 of the lower portion 402 and, and in some examples, beyond the distal end of the lower portion 402. Fastening features such as adhesives and/or interference fitting may be provided to keep the portions 400, 402. One of the benefits of the two-piece button is in manufacturing, where the lower housing 402 may be affixed to the delivery device with minimal design changes to the manufacturing processes and equipment and the proximal portion 400 may be added separately, such as, for example, at the manufacturing site or later by a patient as an attachable module.

Referring next to FIG. 13, an electronic control system 500 is provided for use with any of the corresponding dose detection system described herein, although the embodiment of device 210 is described as the example device. Control system 500 may communicate with the rotational sensor of dose detection system to receive information regarding the sensed rotation of dose setting member 230 relative to housing 212, actuator 250, and/or another component of medication delivery device 210. Control system 500 may use the information from the rotational sensor to determine the amount of medication delivered from medication delivery device 210. The illustrative control system 500 includes a microcontroller unit (MCU) 502 located onboard housing 212 of medication delivery device 210. However, the location of MCU 502 may vary. For example, when control system 500 is adapted for use with the detection sensor system 284, MCU 502 may be located on actuator 250 of medication delivery device 210.

Controller MCU includes at least one processor (e.g., microprocessor) that executes software and/or firmware stored in memory of the controller. The software/firmware code contains instructions that, when executed by processor, causes the controller to perform the functions of the control logic and steps described herein. The illustrative controller MCU 502 includes a processing core 504, a memory 506 (e.g., internal flash memory, on-board electrically erasable and programmable read-only memory (EEPROM), etc.), a power source 508 (e.g., coin cell battery), and a communication module 510. These components may be mounted to and communicate via the circuit board 325, such as, for example, a flexible printed circuit board (FPCB). MCU 502 communicates with the rotation sensor 286, such as, for example, the electrical position sensing member 302. MCU 502 is operative to perform the operations described herein, including determining the number of units indicative of total angular movement of the dose setting member used to determine the amount of medication delivered from medication delivery device 210 based on the information received from rotational sensor 286. MCU 502 may store the detected amount of units or angular movement and/or medication separately or together in a generated dose record in memory 506. The generated dose record may include time/date stamp, dose delivered amount, battery charge status, error log messages, etc. MCU 502 may also transmit the dose record data representative of detected amount of medication or units or angular movement via communication port 510 to a paired remote device 511, such as a user's computer or smartphone. The information may be transmitted from communication port 510 via a wired or wireless communication protocol, such as a Bluetooth low energy (BLE) wireless communication protocol.

Figure 17:
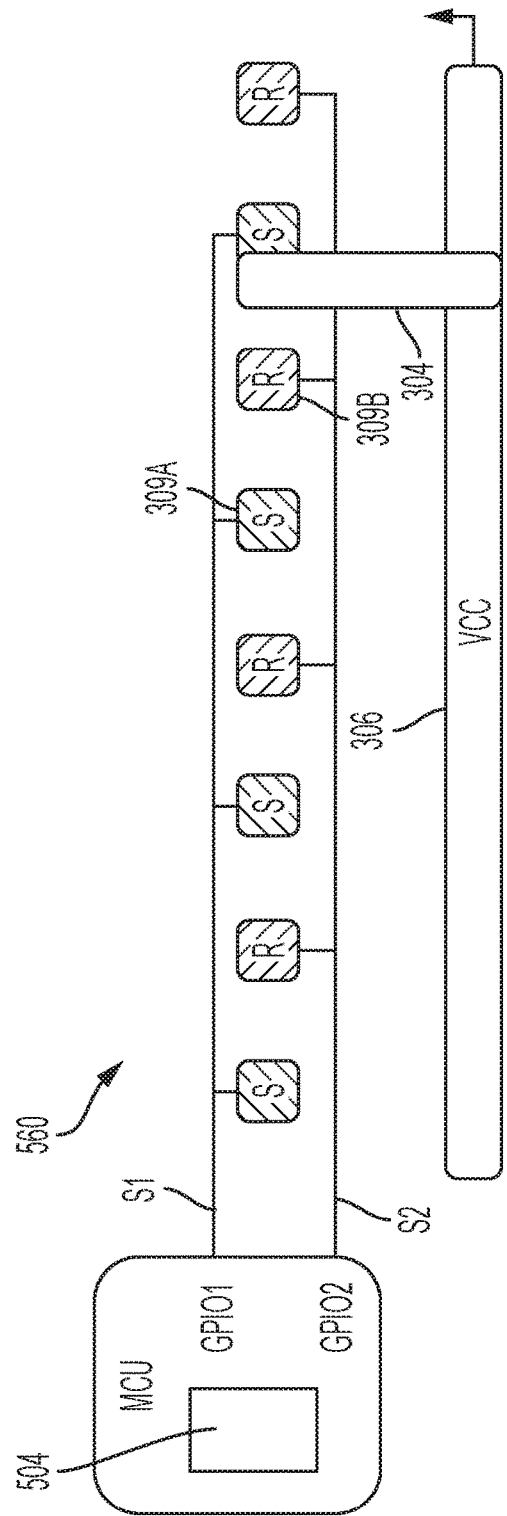
FIG. 17 is a schematic of another example of a dose detection system without a conversion control module.

As described above, the electrical position sensing member of the rotational sensor 286 generates electronically a first signal S1 and a second signal S2. The first signal S1 is generated when the indicator 304 contacts a first 309A of the segmented pads 309 of the first ring 306 and the second ring 308 simultaneously. The second signal S2 is generated when the indicator 304 contacts a second 309B of the segmented pads 309 of the first ring 306 and the second ring 308 simultaneously. In an example shown in FIG. 14, the first segmented pads 309A is coupled to the reset circuit of a latch circuit and the second segmented pads 309B is coupled to the set circuit of the latch circuit. In one embodiment, the controller does not have to be powered on at the start, as the controller may be configured to wake up upon receiving the first of one of the signals S1 or S2. In another example, such as shown in FIG. 17, the first and second signals S1, S2 may be sent directly to the controller, with the controller powered on first, for digital processing (including ADC, filters, and programming) in order to determine the number of dose counts.

A conversion control module 514 may be disposed between the rotational sensor 286 and the processing core 504 of the MCU. The conversion control module 514 is configured to generate an undulating unit signal S3 from the generated first and second signals S1, S2 (that are in an alternating arrangement), which may also be referred to as the set signal S and reset signal R, respectively.

In one example, the conversion control module 514 comprises a latch circuit, and in another example, a SR latch circuit. The latch circuit includes an output signal that will toggle high or low depending on alternating contact input signals received by the latch circuit. The conversion control module 514 is operable to convert the first and second signals S1, S2 into a switch-like, general purpose input/output (GPIO) signal as a single input to the processing core 504 of the MCU. One of the benefits of providing a latch circuit is that the processing power demand may be reduced.

Figure 14:
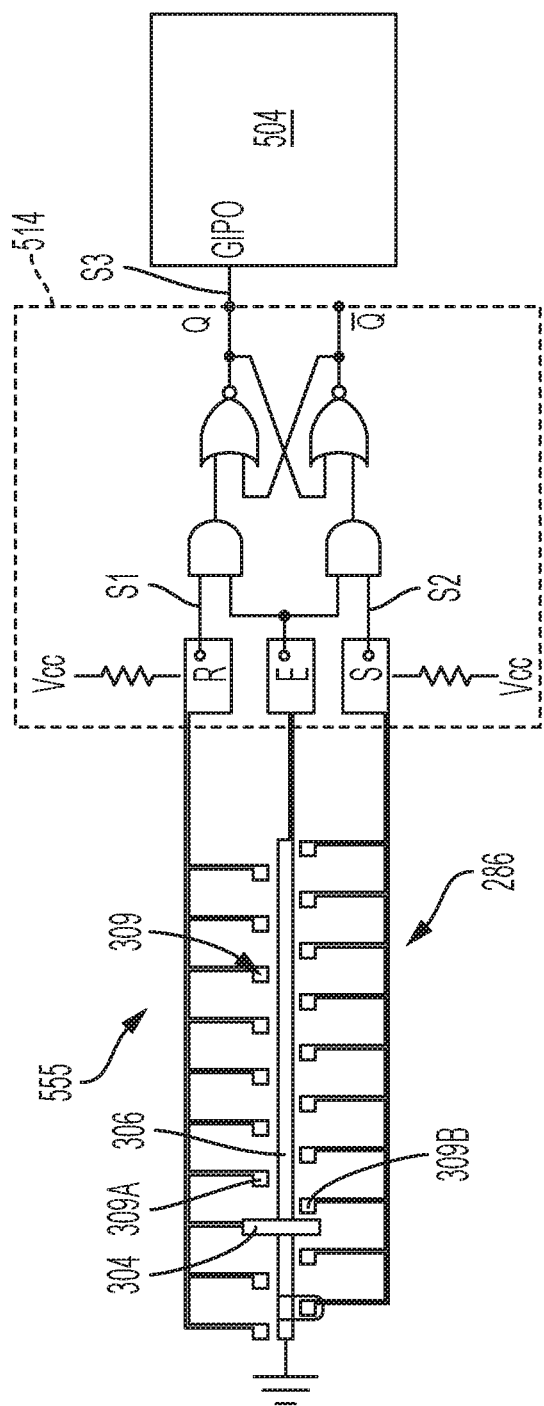
FIG. 14 is a schematic of another example of a dose detection system with an exemplary conversion control module disposed between the dose detection system and a controller of a control system.
Figure 15:
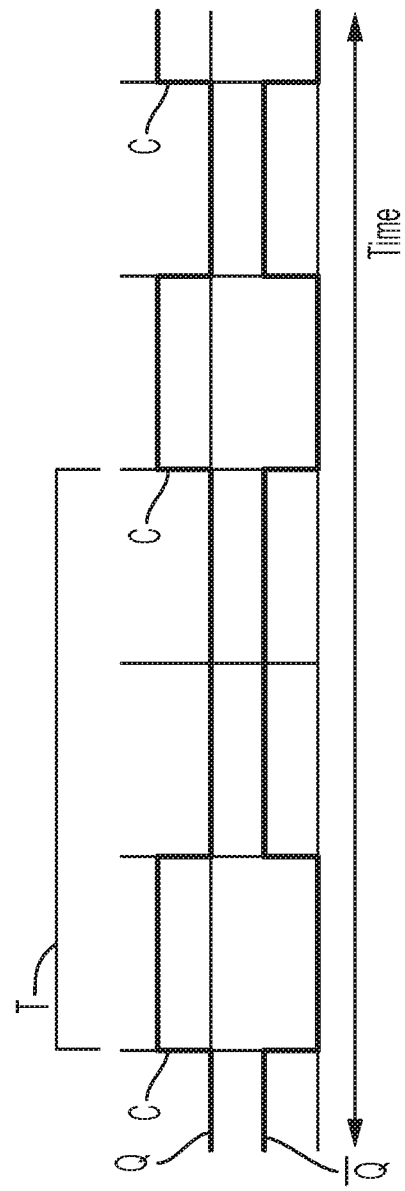
FIG. 15 is a schematic of a control signal generated by the conversion control module that is communicated to the controller of the control system.

FIG. 14 illustratively depicts an example of a detection sensor system 555 with the conversion control module 514, as a SR latch circuit, disposed between the rotational sensor 286 and the processing core 504 of the controller MCU. The position indicator 304 slidably contacts and remains in contact with the ring 306 indicated as ground, while slidably contacting the segmented contact pads 309 to generate the sensing signal. The segmented contact pads 309 are in alternating pattern and divided between the set S and reset R circuits. The latch circuit of the conversion control module 514 is shown to receive the set signal, shown as S2, and the reset R signal, shown as S1, and the ground signal and flip-flop between set and reset to generate Q and not-Q signals, which an example of the Q and not-Q signals is shown in FIG. 15. The processing core 504 of the MCU 502 is operable to receive and process the Q signal, now shown as S3, in order to determine the units of rotation based on the number of rises C or toggled to set in the Q signal, which may be stored in memory. In addition to, or alternative to, the units of rotation may also be determined based on the number of falling edges or toggled to reset in the Q signal, which may be then stored in memory. The dose counts may be stored in memory by the processing core prior to the step of determining the units of rotation. The not-Q signal may be used as a contingent signal, providing the control system with redundancy functionality in case the Q signal's expected pattern fails to demonstrate. In other embodiments, the not-Q signal may be disregarded if sent to the processing core or may be omitted from the processing core. The system 555 may only require one GPIO input. One of the advantages of system 555 is that each unit is counted once. Another of the advantages is that system 555 is configured to avoid repeat dose counts if contact arm contacts same pad on next dosing. System 555 may be independent of dosing speed and/or dosing variability.

Another of the advantages of system 555 is that it acts as a robust debounce circuit. That is, if there is a non-uniform signal coming into system 555, because of the latching functionality, if signal S1 is seen repeatedly, there will be no state change, as this will only occur once there is a signal from S2. The reason systems described herein are better than simply using a debounce circuit or using software debounce is because the amount of debounce a non-uniform signal might need is dependent on the frequency of the signal. If the non-uniform signal's frequency is high, and the debounce is set high, then the multiple signals are blurred together and the controller determines a dose count that is less than expected. Similarly, if the non-uniform signal's frequency is low, and the debounce is set low, the controller determines a dose count that is higher than expected. Additionally, because of the presence of alternating signals, when the diameter of ring 306 is small, the systems described herein may improve upon the mechanical tolerances of the system. For example, with only one signal, the position indicator 304 might maintain contact when moving along pads 309A and 309B, and the controller may not be able to differentiate the signal at 2 clicks.

In another embodiment, an event log module 516 may be disposed between the conversion control module 514 and the processing core 504 of the MCU. The event log module 516 is configured to determine the number of units by counting and logging the number of rising edges and/or falling edges of the single input signal, such as the number times to toggle to set or rises C of the Q signal in FIG. 15. The total number of rising edges in the generated signal S3 is correlated to a total number of units, which is representative of an amount of rotation of the dose member. Alternatively, the event log module may count both of the rising edges and the falling edges to make an amount of rotation determination. The event log module 516 is operable to communicate the determined total number of counts C to the processing core 504 of the MCU 502. In a further example, the processing core 504 of the MCU is configured to power on or wake up the system from a lower power state to a high power state based on receiving the first count from the single input signal. When the system is in the low power state configuration, the event log module 516 has sufficient power to determine at least the initial one of a number of units.

In another embodiment, a time delay module 518 may be in communication with the event log module 516 and a timer, shown as a real-time clock RTC. The time delay module 518 is operable to determine the amount of time elapsed T between rising edges C of the event log module. In one example, the event log module may operate when the controller is in a low power state. Once dosing is complete based on the time delay block, the controller can wake up, receive the signals from the event log module, and store data of dosing information into memory. The amount of time selected for elapsed time since the last count of signals for the time delay block, for example, three seconds, may be used to power on the controller to communicate with the event log module after the dose dispensing operation, thereby reducing the power demand from the power source 508. After this, MCU 502 can immediately turn off and wait at another time, such as when paired to an external device, to communicate one or more dose records data of the dose amount. Alternatively, the amount of time selected, for example, three seconds, can be beneficial to power off the controller after the elapsed time in order to reduce the power demand from the power source 508. After a period of time T has expired from a time of a last of the units determined by the event log module, the system is configured to go into the low power state configuration. The amount of time selected can be beneficial to trigger a communication send of data to an external source prior to a power off command from the processing core 504 of the MCU.

Figure 18:
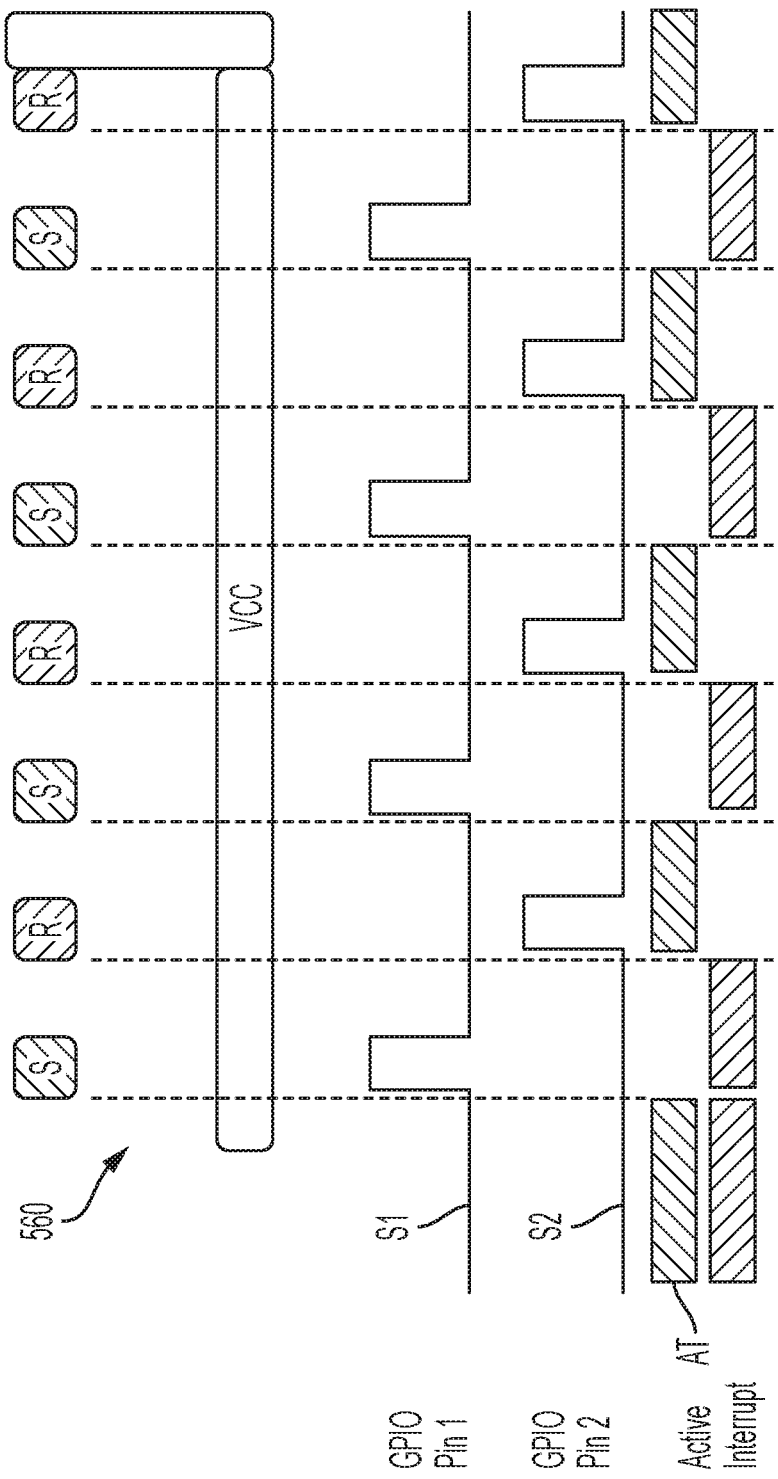
FIG. 18 is a schematic of control signals generated by the system of FIG. 17.

FIG. 17 depicts an alternative detection sensor system 560 with the first and second signals S1, S2, that are different contact input signals, being sent directly to the processing core 504 of the controller MCU on separate GPIO pins. The conversion control module described herein is achieved functionally through software instructions programmed in the processing core and memory. The position indicator 304 slidably contacts and remains in contact with the ring 306 indicated as positive supply voltage (Vcc), while slidably contacting the alternating segmented contact pads 309A, 309B to generate the first and second sensing signals. The segmented contact pads 309A, 309B are divided between the set S circuit and the reset R circuit. The processing core 504 is shown to receive the set signal, shown as S1, as a first GPIO1 input signal and the reset R signal, shown as S2, as a second GPIO2 input signal. FIG. 18 illustrates an example of the GPIO1 signal S1 and GPIO2 signal S2 of system 560 which alternate and interrupts are actively tracked, referred to as AT, and logged by the processing core. The MCU is operable to receive and process the GPIO1 and GPIO2 signals, and determine a number of active interrupts AT in one or both the signals in order to determine the units of rotation based on active interrupts AT that alternate to replicate flip flop functionality. The determined units of rotation may be stored in memory. The dose counts may be stored in memory by the processing core prior to the step of determining the units of rotation. One of the advantages of system 560 is that each unit is counted once. It may be less expensive in manufacturing and/or operational costs than the system with the latch circuit hardware. Another of the advantages is that system 560 is configured to avoid repeat dose counts if contact arm contacts same pad on next dosing. System 560 may be independent of dosing speed and/or dosing variability.

Figure 19A:
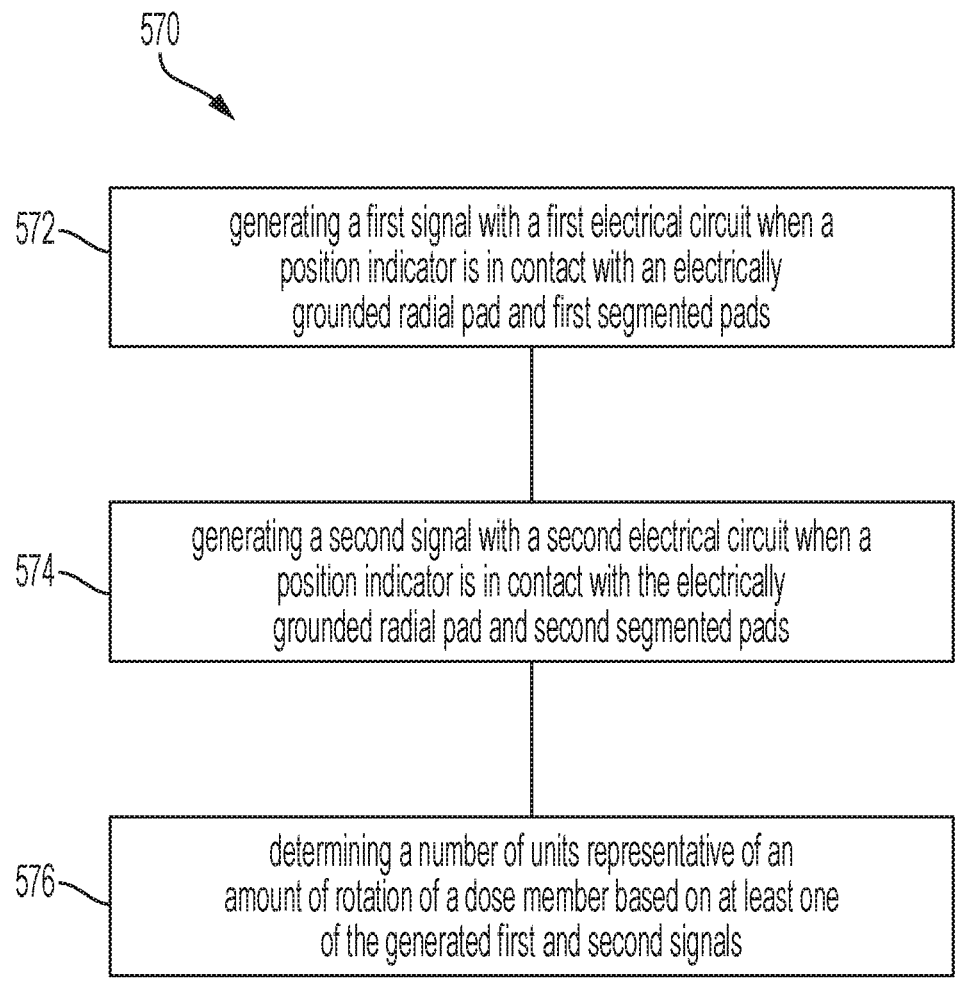
FIG. 19A is a block diagram of the controls logic for dose detection.

FIG. 19A is a flow diagram describing exemplary software logic for dose detection (referred to as 570) based on the hardware interface of any one of the detection sensor system described herein. Processing core executes software and/or firmware stored in memory of controller MCU that contains instructions that, when executed by processing core, causes the controller MCU to perform the functions of the control algorithm described herein. The controller is configured to perform one or more of the following steps. Generating a first signal with the first electrical circuit when the position indicator is in contact with the electrically grounded radial pad and the first segmented pads (at step 572). Generating a second signal with the second electrical circuit when the position indicator is in contact with the electrically grounded radial pad and the second segmented pads (at step 574). Determining a number of units representative of an amount of rotation of the dose member based on at least one of the generated first and second signals (at step 576). One or more of the following steps may be included. Generating an undulating unit signal from the generated first and second signals with a latch circuit. Determining, with an event log module of the controller, a number of rising edges, falling edges, or both of the generated undulating unit signal. Determining a number of active interrupts of at least one of the generated first and second signals. Determining a number of units representative of an amount of rotation of the dose member based on the determined number of active interrupts.

Figure 19B:
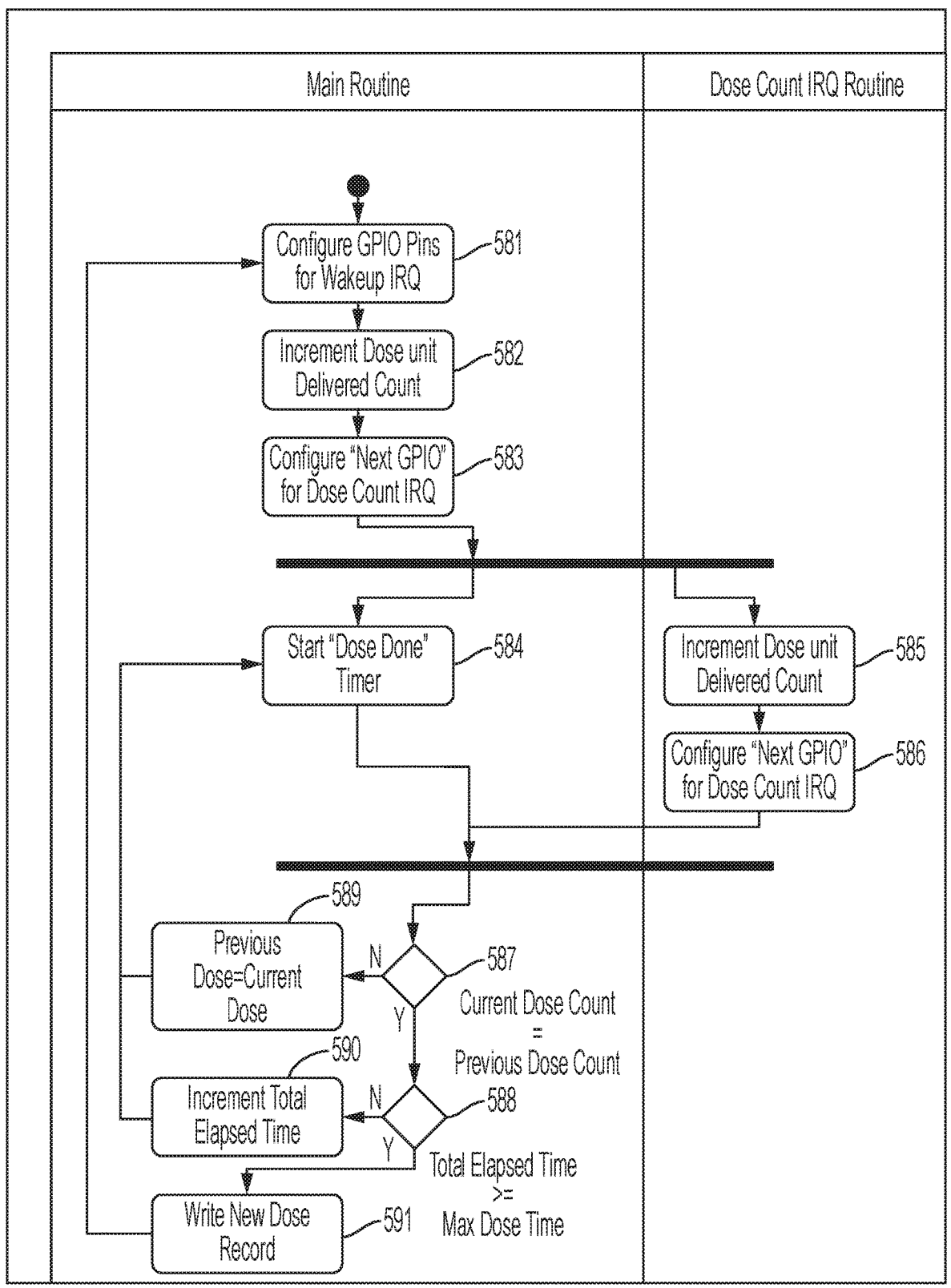
FIG. 19B is a block diagram of the controls logic for the system of FIG. 17.

FIG. 19B is a flow diagram describing the software logic for dose counting (referred to as 580) based on the hardware interface of a detection sensor system of, for example, shown in FIG. 17. Processing core executes software and/or firmware stored in memory of controller MCU. The software/firmware code contains instructions that, when executed by processing core, causes the controller MCU to perform the functions of the control algorithm described herein, such as to provide one or more active interrupts to one or both of the first and second signals to determine the number of units of rotation for dose count.

FIG. 19B describes the main routine in which active interrupts can be implemented by the dose count IRQ routine in order to ignore the noise produced by one of the input first and second signals. It is understood that some of or all of the described steps may be performed. At the beginning of the routine, both GPIO1 and GPIO2 pins are configured to wake up the processing core 504 of MCU from low power state (at step 581). Once a signal (one of signal S1 or signal S2) is received and the processing core 504 of MCU is powered on from low power state, the dose count is increased by one (at step 582) to account for the initial signal (the one of signals S1 or S2). There following, the GPIO that was active (for example, GPIO1 is active for the initial signal S1) is then told to be ignored, and the Next GPIO is held active (at step 583) (for example, GPIO2 is now active). If there is a signal on the Next GPIO (for example, signal S2 on GPIO2) and the dose done timer is started (at step 584), the dose count is increased by one (at step 585). Then, the previous GPIO (for example, GPIO2) is now ignored, and the Next GPIO (the other GPIO now GPIO1) is now configured active for dose count (at step 586). Steps 585 and 586 may provide active interrupts. Then, the current dose count is compared with the previous dose count (at step 587). If the current dose count does not equal the previous dose count, then the current dose becomes the previous dose for the next dose count (at step 589). After step 589, the steps 584, 585 and 586 recycle through to count the next increments of dose units delivered until current dose count equals the previous dose count, that is, there is no more rotation of the dose setting member for the dose detection system to count. Next, there is a timer function to insure the dose delivery is indeed stopped. For example, when the current dose count equals the previous dose count, then the total elapsed time is compared with the max dose time (at step 588). If the total elapsed time is less than the max dose time, then increment total elapsed time is determined (at step 590). When the total elapsed time is greater than or equal to the max dose time, that is, sufficient time has elapsed between the last incremental dose counted, then a new dose record is generated by writing or storing into the memory of the MCU (at step 591). As described herein, new dose record and/or previously stored dose records may be indicated by a display and/or communicated to an external device when paired or linked.

The processing core 504 of MCU will continue to behave in the fashion until the dose done timer hits a certain threshold in between GPIO events when total elapsed time is greater than equal to the max dose time (at step 588). In this case the New Dose Record will be stored. Based on FIG. 19B, once a signal from S1 is recorded, the active interrupt will be turned off, meaning nothing will be recorded from this GPIO1 until there is a signal read by S2. In which case, once S2 is recorded, GPIO2's active interrupt will be deactivated, while GPIO1's active interrupt will be reactivated.

Figure 20:
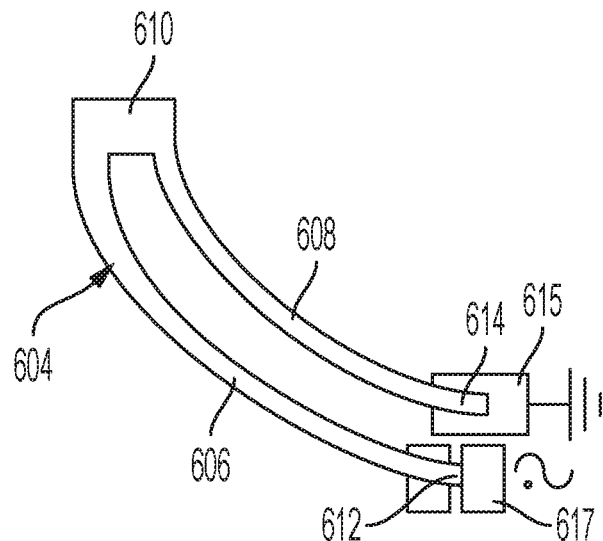
FIG. 20 depicts another embodiment of a position indicator for any of the dose detection systems described herein.

FIG. 20 illustrates an alternative configuration of the position indicator, now referred to as 604. The position indicator 604 includes a first finger 606 and a second finger 608. The first and the second fingers 604, 606 are shown interconnected at a base 610 that is coupled to the indicator base, such as for example, base 312. The tip 612 of the first finger 606, opposite the base 610, is configured to electrically contact one of the continuous contact pad 615 or segmented contact pad 617. The tip 614 of the second finger 608, opposite the base 610, is configured to electrically contact the other of the continuous or segmented contact pads 615, 617. With additional reference to FIG. 9 for general configuration of the position indicator, the base 610 of the indicator 604 may be coupled to the indicator base portion, such as base 312 that is coupled to the dose member, such that the fingers 606, 608 extend proximally away from the dose member. One of the benefits of this configuration is the ability to tune the resiliency, shape and size of the fingers for contacting the pads. Alternatively, in FIG. 22, the first finger 806 and the second finger 808 of the position indicator, referred to now as 804, may extend from the indicator base 812, circumferentially offset from one another, such that the fingers 806, 808 extend along different circumferential locations. Here, the first finger 806 is disposed radially to contact one of the continuous contact pad or segmented contact pad, and the second finger 808 is disposed radially offset from the first finger 808 to contact the other of the continuous contact pad or segmented contact pad. The tips of the arms 806, 808 are shown to include a domed surface 817. The fingers would still be electrically coupled to one another at the indicator base 812. Base 812 is shown having a full ring shape, and including mounting holes 815 formed therein for attachment to the dose setting member, such as the flange. FIG. 23 illustrates the position indicator, referred to as 804', with a semi-ring shaped base 820.

Figure 21:
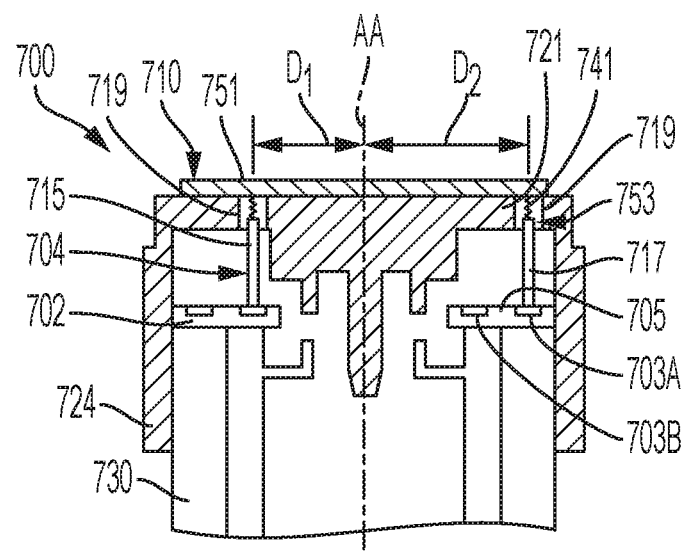
FIG. 21 is a partial, cross-sectional view of a dose detection system according to another embodiment disposed within the proximal portion of any one of the medication delivery devices described herein.

FIG. 21 illustrates an alternative configuration of the dose detection system, referred now to as 710, of another medication delivery device 700. The device 710 includes many of the same components that are operational for dose setting and dose dispensing as described with reference to the device 10, including at least a portion of the electronic components in the electronics assembly, and such components will have the same corresponding descriptions. The device 700 includes the device body disposed about the longitudinal axis AA. The dose member 730 is coupled to the device body and rotatable relative to the device body during the dose setting operation. The actuator is coupled to the device body and movable relative to the device body during the dose dispensing operation. The detection system 710 is configured to detect rotation of the dose member 730 during the dose dispensing operation. The detection system 710 includes the electrical position sensing member 702 and the position indicator 704 engageable with the electrical position sensing member. The position indicator 704 is configured to electrically contact with the electrical position sensing member during the dose dispensing operation and generate first and second signals indicative of the incremental position of the position indicator along the electrical position sensing member. The control system in communication with the position indicator 704. The control system includes the MCU and the conversion control module configured to convert said first and second position signals, which can be analog signals, to an undulating signal, which can be a digital signal. The control system is programmed to determine a number of units of rotation of the dose member based on the undulating signal.

The electrical position sensing member 702 is disposed distal to the position indicator 704. The sensing member 702 is coupled to the dose member 730, such as the flange 738, in a rotationally and axially fixed manner. One or more electrical contact pads, a continuous pad 703A and a segment pad 703B, can be disposed along a button facing side 705 of the sensing member 702. As described above, the continuous pad 703A may be disposed radially outward to the segment pad 703B, or vice versa. As shown, the position indicator 704 includes pins for sensing, shown as a first pin 715 and a second pin 717, which are received through housing apertures 719 defined by the wall 721 of lower portion 724. Each of the pins 715, 717 is positioned to have a distal contact tip 725 that is capable of resting against the corresponding contact pad 703A, 703B. The first pin 715 may be in contact with the segmented pad 703B and the second pin 717 may in contact with the continuous pad 703A. The first pin is positional radially from the longitudinal axis AA by a first distance D1, and the second pin is positional radially from the longitudinal axis AA by a second distance D2, which is larger than the first distance D1. Each of the pins 715, 717 may be biased, such as a coil spring 741 that is positioned between the lower housing portion 724 and each of the pins 715, 717 to bias the pin outward in the distal direction in a position to so that the tip contacts the contact pads. The spring 741 is shown disposed between the lower housing and the end of the pin; however, the spring may disposed along the pin shaft or other places. The pin is in electrical communication with the circuit board 751 via a pin module 753 such that the pin is operational to generate signals. The pin module 753 is configured to house the end of the pin the spring, as well as function as an electrical path to generate the sensing signals.

As described above, the sensed rotation of dose setting member may be used to determine to the amount of medication delivered from medication delivery device. In certain embodiments, each rotation of the position indicator that is coupled to the dose setting member across the respective contact sensing pads of the electrical position sensing member that is coupled to the actuator may correlate with one dose unit or a unit of rotation, or some fraction thereof. Thus, based on information received from electrical position sensing member, dose detection system may incrementally dose count from start to finish the number of times position indicator rotates across electrical position sensing member and may correlate that number with the amount of medication delivered from medication delivery device. However, the size, shape and spacing of the contact pads of each electrical position sensing member may vary to correlate with other dose units.

In certain embodiments, control system 500 may be configured to distinguish the direction of rotation of dose setting member. For example, control system 500 may be configured to distinguish whether the dose setting member is rotating in a first direction during the dose setting operation or in a second direction during the dose dispensing operation. For purposes of determining the amount of medication actually delivered from any one of the medication delivery devices described herein, control system 500 may ignore the rotation of the dose setting member during the dose setting operation and only process the rotation of the dose setting member during the actual dose dispensing operation. Control system 500 may distinguish these directions using phase shifts or shift register coding, for example.

A method of determining an amount of dose dispensing with any one of the delivery devices described herein. In one embodiment, a first signal is generated with a first electrical circuit when the position indicator is in contact with the continuous radial pad and the first segmented pads. A second signal is generated with a second electrical circuit when the position indicator is in contact with the continuous radial pad and the second segmented pads. A number of units is representative of an amount of rotation of the dose member is determined by the control system based on at least one of the generated first and second signals. In one embodiment, an undulating unit signal may be generated from the generated first and second signals with a conversion control module, such as, for example, a latch circuit. An event log module of the control system may be used to determine a number of rising edges, falling edges, or both of the generated undulating unit signal such that the number of units is based on the determined number. In another embodiment, the control system may determine a number of active interrupts of at least one of the generated first and second signals, and determine the number of units that is representative of an amount of rotation of the dose member based on the determined number of active interrupts.

The alternating circuit signals generated from the position indicator in contact with the first segmented sensor pads and the ground pad, and in contact with the second segmented sensor pads and the ground pad, along with the conversion means to determine an amount rotation of the dose member based on at least one of the alternating circuit signals can provide more accurate and reliable determination of the amount of rotation. It can avoid issues with debounce and noise issues within the input signal that can allow for miscounts of units. Resynchronization of the detection system can also be omitted.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Various aspects are described in this disclosure, which include, but are not limited to, the following aspects:

1. A delivery device, including: a dose member rotatable during a dose dispensing event; a detection system including a position indicator, a position sensing member, a first electrical circuit and a second electrical circuit, one of the position indicator and the position sensing member coupled to the dose member, the position sensing member including a segmented radial pad and an electrically grounded radial pad disposed radially relative to one another along an axial surface of the position sensing member, the segmented radial pad including a plurality of first segmented pads and a plurality of second segmented pads, the first and second segmented pads disposed in an alternating pattern, wherein the first electrical circuit is configured to generate a first signal in response to the position indicator being in a contacting relationship with the first segmented pads and the electrically grounded radial pad, and the second electrical circuit is configured to generate a second signal in response to the position indicator being in a contacting relationship with the second segmented pads and the electrically grounded radial pad; and a controller in communication with the first and second electrical circuits, and operable to determine a number of units of rotation of the dose member based on, directly or indirectly, at least one of the generated first and second signals.

2. The device of aspect 1, wherein the controller is configured to receive both of the generated first and second signals, and to determine a number of active interrupts of at least one of the generated first and second signals to determine the number of units.

3. The device of any one of aspects 1-2, wherein the controller includes a conversion control module operably coupled to each of the first and second electrical circuits, and a processing core operably coupled to the conversion control module, wherein the conversion control module is configured to generate an undulating unit signal from the generated first and second signals, wherein the processing core is configured to determine the number of units of rotation based on a number of rising edges, falling edges, or both of the generated undulating unit signal.

4. The device of aspect 3, wherein the conversion control module includes a latch circuit.

5. The device of aspect 3, wherein the controller includes an event log module operably coupled between the conversion control module and the processing core, wherein the event log module is configured to count the number of rising edges, falling edges, or both of the generated undulating unit signal.

6. The device of aspect 5, wherein the event log module is configured to count the number of rising edges, falling edges, or both of the generated undulating unit signal when the processing core is in a lower power state, wherein, in response to an expiration of a period of time from a determination of a last count from the generated undulating unit signal by the event log module, the controller is configured to power on the processing core from the lower power state to receive the generated undulating unit signal from the even log module.

7. The device of any one of aspects 1-6, wherein the position indicator is coupled to the dose member.

8. The device of aspect 7, wherein the position indicator includes a base coupled to the dose member, one or more arms extending from the base, the arm being biased away from the dose member, and a contacting portion configured to contact both of the segmented radial pads and the electrically grounded radial pads simultaneously.

9. The device of aspect 7, wherein the position indicator includes a base coupled to the dose member, more than one arm extending from the base, the arm being biased away from the dose member, one of the arms including a contacting portion configured to contact one of the segmented radial pads and the electrically grounded radial pads, and another one of the arms including a contacting portion configured to contact the other of the segmented radial pads and the electrically grounded radial pads simultaneously with the contacting of the other arm.

10. The device of aspect 7, further including a button, wherein the button houses the position sensing member that is disposed proximal to the position indicator, wherein, during a dose setting event, the dose member is rotationally coupled to the button such that the dose member and the button, and thus the position indicator and the position sensing member, rotate together relative to a device body, and, during the dose dispensing event, the dose member is rotationally uncoupled from the button such that the dose member rotates relative to the button that is rotationally fixed, and thus the position indicator rotates relative to the position sensing member that is rotationally fixed.

11. The device of any one of aspects 1-10, further including a button, wherein the position sensing member is coupled to the dose member, and the button houses the position indicator that is disposed proximal to the position sensing member, wherein, during a dose setting event, the dose member is rotationally coupled to the button such that the dose member and the button rotate together relative to a device body, and, during the dose dispensing event, the dose member is rotationally uncoupled from the button such that the dose member rotates relative to the button.

12. The device of any one of aspects 1-11, wherein the controller is configured to provide one or more active interrupts to one or both of the first and second signals to determine the number of units of rotation.

13. The device of aspect 12, wherein the controller includes a first input coupled to the first electrical circuit and a second input coupled to the second electrical circuit, the controller configured to: start a dose done timer based on activation of the first input and ignoring the second input; determine an increment of a dose unit delivered count based on the first signal from the activated first input; and provide an active interrupt to the first signal by activating the second input and ignoring the first input to determine the number of units of rotation based on the second signal from the activated second input.

14. A delivery device, including: a device body having a longitudinal axis; a dose member coupled to the device body and rotatable relative to the device body during a dose dispensing event; a button coupled to a proximal end of the device body and movable relative to the device body during the dose dispensing event, the button including an upper housing and a lower housing distal to the upper housing; and a detection system configured to detect rotation of the dose member during the dose dispensing event, the detection system including a position sensing member housed within the lower housing, a position indicator coupled to the dose member, the position sensing member including a plurality of first segmented pads and a plurality of second segmented pads arranged radially in an alternating pattern along an axial surface of the position sensing member, and a continuous radial pad disposed along the axial surface, radially relative to the first and second segmented pads, the position indicator radially sized to contact the continuous radial pad and one of the first and second radial pads simultaneously, and, during the dose dispensing event, the position sensing member is configured to generate a first signal when the position indicator is in contact with the continuous radial pad and the first segmented pads, and a second signal when the position indicator is in contact with the continuous radial pad and the second segmented pads, and a controller operable to determine a number of units representative of an amount of rotation of the dose member based on, directly or indirectly, at least one of the generated first and second signals.

15. The device of aspect 14, wherein a wall at least partially separates an upper cavity defined by the upper housing and a lower cavity defined by the lower housing, wherein the controller includes a power source and a processing core each housed within the upper cavity of the upper housing of the button.

16. The device of aspect 15, wherein the lower housing includes a mounting collar securely coupled to a component of the dose member, wherein, during a dose setting event, the dose member is rotationally coupled to the button such that the dose member and the button rotate together relative to the device body, and, during the dose dispensing event, the dose member is rotationally uncoupled from the button such that the dose member rotates relative to the button.

17. The device of any one of aspects 14-16, wherein the position indicator includes a first electrical circuit operable to generate the first signal and a second electrical circuit operable to generate the second signal, and wherein the controller includes a latch circuit operably coupled to each of the first and second electrical circuits, the latch circuit disposed between the position indicator and the processing core, wherein the latch circuit is configured to generate an undulating unit signal from the first and second signals, wherein the processing core is configured to determine the number of units based on a number or rising edges, falling edges, or both of the generated undulating unit signal.

18. The device of aspect 17, wherein the controller includes an event log module operably coupled between the latch circuit and the processing core, wherein the event log module is configured to determine the number of units based on a count of rising edges, falling edges, or both of the generated undulating unit signal, and to communicate the number of units to the processing core, wherein, in response to an expiration of a period of time from a determination of a last count from the generated undulating unit signal by the event log module, the controller is configured to set the device into a low power state configuration.

19. The device of any one of aspects 14-18, wherein the controller is configured to receive both of the generated first and second signals, determine a number of active interrupts of at least one of the generated first and second signals, determine the number of units based on the number of active interrupts.

20. A method of determining an amount of dose dispensing with a delivery device, the delivery device including a position indicator and a position sensing member, one of the position indicator and the position sensing member coupled to the dose member, the position sensing member including a segmented radial pad and an electrically grounded radial pad disposed radially relative to one other along an axial surface of the position sensing member, the segmented radial pad including a plurality of first segmented pads and a plurality of second segmented pads disposed in an alternating pattern, wherein the position indicator is radially sized to contact the first segmented pads and the electrically grounded radial pad, and the position indicator is radially sized to contact the second segmented pads and the electrically grounded radial pad, the first segmented pads coupled to a first electrical circuit and the second segmented pads coupled to a second electrical circuit, at least one of the first and second electrical circuits coupled to a controller, the method including:
generating a first signal with the first electrical circuit when the position indicator is in contact with the electrically grounded radial pad and the first segmented pads; generating a second signal with the second electrical circuit when the position indicator is in contact with the electrically grounded radial pad and the second segmented pads; and determining, with the controller, a number of units representative of an amount of rotation of the dose member based on at least one of the generated first and second signals.

21. The method of aspect 20, further including: generating an undulating unit signal from the generated first and second signals with a latch circuit; and determining, with an event log module of the controller, a number of rising edges, falling edges, or both of the generated undulating unit signal, wherein the determining step further includes determining, with the controller, a number of units representative of an amount of rotation of the dose member based on the determined number.

22. The method of any one of aspects 20-21, further including: determining, with the controller, a number of active interrupts of at least one of the generated first and second signals, wherein the determining step further includes determining, with the controller, a number of units representative of an amount of rotation of the dose member based on the determined number of active interrupts.

A device of any one of the preceding aspects, further comprising a container, and a medication disposed within the container and expelled from the container during the dose dispensing event.

What is claimed:

1. A delivery device, comprising:
    a dose member rotatable during a dose dispensing event;
    a detection system including an electrical contact, a position sensing member, a set electrical circuit and a reset electrical circuit, one of the electrical contact and the position sensing member coupled to the dose member, the position sensing member including a segmented radial pad and an electrically grounded radial pad disposed radially relative to one another along an axial surface of the position sensing member, the segmented radial pad comprising a plurality of first segmented pads and a plurality of second segmented pads, the plurality of first segmented pads and the plurality of second segmented pads disposed in an alternating pattern, wherein the set electrical circuit is configured to generate a set signal in response to the electrical contact being in a contacting relationship with the electrically grounded radial pad and at least one of the plurality of first segmented pads, and the reset electrical circuit is configured to generate a reset signal in response to the electrical contact being in a contacting relationship with the electrically grounded radial pad and at least one of the plurality of second segmented pads; and
    a controller in communication with the set electrical circuit and the reset electrical circuit, and operable to determine a number of units of rotation of the dose member based on, directly or indirectly, at least one of the set signal and the reset signal, wherein the controller includes:
        a conversion control module comprising a latch circuit operably coupled to each of the set electrical circuit and the reset electrical circuit, the latch circuit configured to generate an undulating unit signal that is set to one of a logic high or a logic low state when the latch circuit receives the set signal from the set electrical circuit, and that is reset to the other of the logic high or the logic low state when the latch circuit receives the reset signal from the reset electrical circuit, and
        a processing core operably coupled to the conversion control module configured to determine the number of units of rotation based on a number of rising edges, falling edges, or both of the generated undulating unit signal.

2. The delivery device of claim 1, wherein the controller is configured to receive both the set signal and the reset signal, and to determine a number of active interrupts of at least one of the set signal and the reset signal to determine the number of units of rotation.

3. The delivery device of claim 1, wherein the controller includes an event log module operably coupled between the conversion control module and the processing core, wherein the event log module is configured to count the number of rising edges, falling edges, or both of the undulating unit signal.

4. The delivery device of claim 3, wherein the event log module is configured to count the number of rising edges, falling edges, or both of the undulating unit signal when the processing core is in a lower power state, wherein, in response to an expiration of a period of time from a determination of a last count from the undulating unit signal by the event log module, the controller is configured to power on the processing core from the lower power state to receive the number of rising edges, falling edges, or both of the undulating unit signal from the event log module.

5. The delivery device of claim 1, wherein the electrical contact is coupled to the dose member.

6. The delivery device of claim 5, wherein the electrical contact comprises a base coupled to the dose member, one or more arms extending from the base, the one or more arms being biased away from the dose member, and a contacting portion configured to simultaneously contact the electrically grounded radial pad and (i) at least one of the plurality of first segmented pads, or (ii) at least one of the plurality of second segmented pads.

7. The delivery device of claim 5, wherein the electrical contact comprises a base coupled to the dose member, more than one arm extending from the base, the more than one arm being biased away from the dose member, one of the more than one arm including a contacting portion configured to contact the electrically grounded radial pad and (i) one of the plurality of first segmented pads or (ii) one of the plurality of second segmented pads, and another one of the more than one arm including a contacting portion configured to contact the electrically grounded radial pad and the other of (i) one of the plurality of first segmented pads or (ii) one of the plurality of second segmented pads.

8. The delivery device of claim 5, further comprising a button, wherein the button houses the position sensing member that is disposed proximal to the electrical contact, wherein, during a dose setting event, the dose member is rotationally coupled to the button such that the dose member and the button, and thus the electrical contact and the position sensing member, rotate together relative to a device body, and, during the dose dispensing event, the dose member is rotationally uncoupled from the button such that the dose member rotates relative to the button that is rotationally fixed, and thus the electrical contact rotates relative to the position sensing member that is rotationally fixed.

9. The delivery device of claim 1, further comprising a button, wherein the position sensing member is coupled to the dose member, and the button houses the electrical contact that is disposed proximal to the position sensing member, wherein, during a dose setting event, the dose member is rotationally coupled to the button such that the dose member and the button rotate together relative to a device body, and, during the dose dispensing event, the dose member is rotationally uncoupled from the button such that the dose member rotates relative to the button.

10. The delivery device of claim 1, wherein the controller is configured to provide one or more active interrupts to one or both of the set signal and the reset signal to determine the number of units of rotation.

11. The delivery device of claim 10, wherein the controller includes a first input coupled to the set electrical circuit and a second input coupled to the reset electrical circuit, the controller configured to:
    start a dose done timer based on activation of the first input and ignoring the second input;
    determine an increment of a dose unit delivered count based on said set signal from the first input; and
    provide one of the one or more active interrupts to the set signal by activating the second input and ignoring the first input to determine the number of units of rotation based on said reset signal from the second input.

12. The delivery device of claim 1, further comprising a container, and a medication disposed within the container and capable of being expelled from the container during the dose dispensing event.

13. The delivery device of claim 1, further comprising:
    a device body having a longitudinal axis; and
    a button coupled to a proximal end of the device body and movable relative to the device body during the dose dispensing event, the button comprising an upper housing and a lower housing distal to the upper housing;
    wherein the position sensing member is housed within the lower housing of the button.

14. The delivery device of claim 13, wherein a wall at least partially separates an upper cavity defined by the upper housing of the button and a lower cavity defined by the lower housing of the button, wherein the controller further includes a power source, wherein the power source and the processing core are each housed within the upper cavity of the upper housing of the button.

15. The delivery device of claim 14, wherein the lower housing of the button includes a mounting collar securely coupled to a component of the dose member, wherein, during a dose setting event, the dose member is rotationally coupled to the button such that the dose member and the button rotate together relative to the device body, and, during the dose dispensing event, the dose member is rotationally uncoupled from the button such that the dose member rotates relative to the button.

16. The delivery device of claim 3, wherein, in response to an expiration of a period of time from a determination of a last count from the undulating unit signal by the event log module, the controller is configured to set the delivery device into a low power state configuration.

* * * * *